(12) United States Patent
Lee et al.

(10) Patent No.: US 8,198,274 B2
(45) Date of Patent: Jun. 12, 2012

(54) SUBSTITUTED INDOLYL AND INDAZOLYL DERIVATIVES AND USES THEREOF

(75) Inventors: Eun Kyung Lee, San Jose, CA (US); Ryan Craig Schoenfeld, San Jose, CA (US); Robert James Weikert, Boulder Creek, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 9 days.

(21) Appl. No.: 12/460,199

(22) Filed: Jul. 15, 2009

(65) Prior Publication Data

US 2010/0016312 A1    Jan. 21, 2010

Related U.S. Application Data

(60) Provisional application No. 61/080,875, filed on Jul. 15, 2008.

(51) Int. Cl.
| | |
|---|---|
| *A61K 31/5377* | (2006.01) |
| *A61K 31/404* | (2006.01) |
| *A61K 31/4725* | (2006.01) |
| *A61K 31/496* | (2006.01) |
| *A61P 25/22* | (2006.01) |
| *C07D 209/18* | (2006.01) |
| *C07D 209/14* | (2006.01) |
| *C07D 401/10* | (2006.01) |
| *C07D 403/10* | (2006.01) |
| *C07D 413/10* | (2006.01) |

(52) U.S. Cl. ............ 514/235.2; 514/254.09; 514/307; 514/415; 544/143; 544/373; 546/148; 548/469

(58) Field of Classification Search .............. None
See application file for complete search history.

(56) References Cited

U.S. PATENT DOCUMENTS

| 5,086,070 A | 2/1992 | Clemence et al. |
| 2004/0192653 A1 | 9/2004 | Munson et al. |

FOREIGN PATENT DOCUMENTS

| WO | 2005061455 A1 | 7/2005 |
| WO | 2007062996 A1 | 6/2007 |

OTHER PUBLICATIONS

Erion et al., caplus an 2006:1252314.*
Liu et al., caplus an 2009:853517.*
Sharma et al., Tetrahedron Letters, 49, 2008, 7062-7065.*
Wermuth, C. G., "Molecular Variations Based on Isosteric Replacements," The Practice of Medicinal Chemistry, 1996, XP002190259, pp. 203-237.

* cited by examiner

*Primary Examiner* — Sun Jae Loewe
(74) *Attorney, Agent, or Firm* — Robert C. Hall

(57) ABSTRACT

This application discloses compounds of generic Formula I:

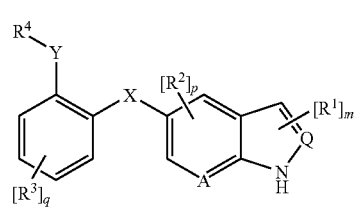

I or pharmaceutically acceptable salts thereof, wherein A, $R^1$, $R^2$, $R^3$, $R^4$, Q, X, Y, m, p, and q are defined as described herein, useful for treatment of diseases associated with monoamine reuptake inhibitors. Also provided are pharmaceutical compositions, methods of using, and methods of preparing the compounds.

12 Claims, No Drawings

SUBSTITUTED INDOLYL AND INDAZOLYL DERIVATIVES AND USES THEREOF

CROSS-REFERENCE TO RELATED APPLICATIONS

This application is entitled to the benefit of U.S. provisional patent application Ser. No. 61/080,875 filed on Jul. 15, 2008, the disclosure of which is incorporated herein by reference.

FIELD OF THE INVENTION

This invention pertains to 4-, 5-, and 6-substituted indolyl, indazolyl, pyrrolyl pyridinyl, and pyrazolyl pyridinyl compounds and methods for using the same. In particular, compounds of the present invention are useful for treatment of diseases associated with monoamine reuptake inhibitors.

BACKGROUND OF THE INVENTION

Psychiatry (2000) 67, 7-11; Resser et al., Depress. Anxiety (2000) 12 (Suppl 1) 2-19; and Hirschfeld et al., J. Clin. Psychiatry (2000) 61, 4-6). In particular, serotonin (5-hydroxytryptamine) and norepinephrine are recognized as key modulatory neurotransmitters that play an important role in mood regulation. Selective serotonin reuptake inhibitors (SSRIs) such as fluoxetine, sertraline, paroxetine, fluvoxamine, citalopram and escitalopram have provided treatments for depressive disorders (Mas and et al., Harv. Rev. Psychiatry (1999) 7, 69-84). Noradrenaline or norepinephrine reuptake inhibitors such as reboxetine, atomoxetine, desipramine and nortryptyline have provided effective treatments for depressive, attention deficit and hyperactivity disorders (Scates et al., Ann. Pharmacother. (2000) 34, 1302-1312; Tatsumi et al., Eur. J. Pharmacol. (1997) 340, 249-258).

Enhancement of serotonin and norepinephrine neurotransmission is recognized to be synergistic in the pharmacotherapy of depressive and anxiolytic disorders, in comparison with enhancement of only serotonin or norepinephrine neurotransmission alone (Thase et al., Br. J. Psychiatry (2001) 178, 234, 241; Tran et al., J. Clin. Psychopharmacology (2003) 23, 78-86). Dual reuptake inhibitors of both serotonin and norepinephrine, such as duloxetine, milnacipran and venlafaxine are currently marketed for treatment of depressive and anxiolytic disorders (Mallinckrodt et al., J. Clin. Psychiatry (2003) 5(1) 19-28; Bymaster et al., Expert Opin. Investig. Drugs (2003) 12(4) 531-543). Dual reuptake inhibitors of serotonin and norepinephrine also offer potential treatments for schizophrenia and other psychoses, dyskinesias, drug addition, cognitive disorders, Alzheimer's disease, obsessive-compulsive behavior, attention deficit disorders, panic attacks, social phobias, eating disorders such as obesity, anorexia, bulimia and "binge-eating", stress, hyperglycemia, hyperlipidemia, non-insulin-dependent diabetes, seizure disorders such as epilepsy, and treatment of conditions associated with neurological damage resulting from stroke, brain trauma, cerebral ischemia, head injury and hemorrhage. Dual reuptake inhibitors of serotonin and norepinephrine also offer potential treatments for disorders and disease states of the urinary tract, and for pain and inflammation.

More recently, "triple reuptake" inhibitors ("broad-spectrum antidepressants") which inhibit the reuptake of norepinephrine, serotonin, and dopamine, have been recognized as useful for the treatment of depression and other CNS indications (Beer et al., J. Clinical Pharmacology (2004) 44:1360-1367; Skolnick et al., Eur J Pharmacol. (2003) February 14;461(2-3):99-104).

Monoamine reuptake inhibitors also have use in pain treatment. Serotonin has been found to have a role in pain processing in the peripheral nervous system and to contribute to peripheral sensitization and hyperalgesia in inflammation and nerve injury (Sommer et al., Molecular Neurobiology (2004) 30(2), 117-125). The serotonin-norepinephrine reuptake inhibitor duloxetine has been shown effective in treatment of pain in animal models (Iyengar et al., J. Pharm. Exper. Therapeutics (2004), 311, 576-584).

There is accordingly a need for compounds that are effective as serotonin reuptake inhibitors, norepinephrine reuptake inhibitors, dopamine reuptake inhibitors, and/or dual reuptake inhibitors of serotonin, norepinephrine and/or dopamine, or triple reuptake inhibitors of norepinephrine, serotonin, and dopamine, as well as methods of making and using such compounds in the treatment of depressive, anxiolytic, genitourinary, pain, and other disorders. The present invention satisfies these needs.

SUMMARY OF THE INVENTION

The application provides a compound of Formula I':

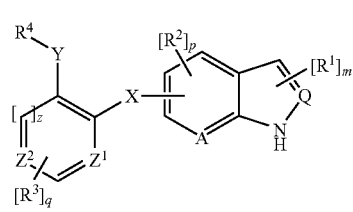

or a pharmaceutically acceptable salt thereof,
wherein:
$Z^1$ is CH, N, or $C(R^3)$;
$Z^2$ is CH, S, or $C(R^3)$;
z is 0 or 1;
X is $CH_2$, CH(OH), or C(O);
Y is $(CH(R^5))_n$ or $O(CH(R^5))_n$;
n is 0, 1, or 2;
Q is CH, $C(R^1)$, or N;
A is CH, $C(R^2)$, or N;
$R^1$ and $R^2$ are each independently CN, $C(O)NH_2$, $S(O)_2R^{1'}$, halogen, lower alkyl, lower haloalkyl, or lower alkoxy;
$R^{1'}$ is H or lower alkyl;
m is 0 or 1;
p is 0, 1, or 2;
$R^3$ is lower alkyl, lower alkoxy, lower haloalkyl, halogen, CN, $C(O)N(R^{1'})_2$, $NHS(O)_2R^{1'}$, or $N(R^{3'})(R^{3''})$;
$R^{3'}$ and $R^{3''}$ are each independently H, lower alkyl, lower haloalkyl, or $R^{3'}$ and $R^{3''}$ together form lower heteroaryl or lower heterocycloalkyl, optionally substituted with lower alkyl, hydroxy, lower alkoxy, lower haloalkyl, or oxo;
q is 0, 1, or 2;
$R^4$ is heterocycloalkyl or $N(R^{4'})(R^{4''})$;
$R^{4'}$ and $R^{4''}$ are each independently H, lower alkyl, lower hydroxyalkyl, lower alkoxyalkyl, lower cycloalkyl, lower haloalkyl;
or $R^{4'}$ and $R^{4''}$ together form lower heteroaryl or lower heterocycloalkyl, optionally substituted with lower alkyl, hydroxy, lower alkoxy, lower haloalkyl, or oxo;

or R$^{4'}$ and R$^3$ together form lower heteroaryl or lower heterocycloalkyl, optionally substituted with lower alkyl, hydroxy, lower alkoxy, lower haloalkyl, or oxo; and each R$^5$ is independently H, lower alkyl, lower alkoxy, lower hydroxyalkyl, or lower haloalkyl;

with the proviso that if X is C(=O), Y is O(CH$_2$)$_2$, z is 1, Z$^1$ is CH, Z$^2$ is CH, m is 0, q is 0, A is CH, Q is CH, and R$^4$ is NH(C(CH$_3$)$_3$), then p is not 0.

The application provides a compound of Formula I:

I or a pharmaceutically acceptable salt thereof,
wherein:
X is CH$_2$, CH(OH), or C(O);
Y is (CH(R$^5$))$_n$ or O(CH(R$^5$))$_n$;
   n is 0, 1, or 2;
Q is CH, C(R$^1$), or N;
A is CH, C(R$^2$), or N;
R$^1$ and R$^2$ are each independently CN, C(O)NH$_2$, S(O)$_2$R$^{1'}$, halogen, lower alkyl, lower haloalkyl, or lower alkoxy;
   R$^{1'}$ is H or lower alkyl;
m is 0 or 1;
p is 0, 1, or 2;
R$^3$ is lower alkyl, lower alkoxy, lower haloalkyl, halogen, CN, C(O)N(R$^{1'}$)$_2$, NHS(O)$_2$R$^{1'}$, or N(R$^{3'}$)(R$^{3''}$);
   R$^{3'}$ and R$^{3''}$ are each independently H, lower alkyl, lower haloalkyl, or R$^{3'}$ and R$^{3''}$ together form lower heteroaryl or lower heterocycloalkyl, optionally substituted with lower alkyl, hydroxy, lower alkoxy, lower haloalkyl, or oxo;
q is 0, 1, or 2;
R$^4$ is N(R$^{4'}$)(R$^{4''}$);
   R$^{4'}$ and R$^{4''}$ are each independently H, lower alkyl, lower hydroxyalkyl, lower alkoxyalkyl, lower cycloalkyl, lower haloalkyl, or R$^{4'}$ and R$^{4''}$ together form lower heteroaryl or lower heterocycloalkyl, optionally substituted with lower alkyl, hydroxy, lower alkoxy, lower haloalkyl, or oxo; and
each R$^5$ is independently H, lower alkyl, lower alkoxy, lower hydroxyalkyl, or lower haloalkyl.

In certain embodiments of Formula I, X is CH$_2$.
In certain embodiments of Formula I, Q is CH.
In certain embodiments of Formula I, A is CH.
In certain embodiments of Formula I, p is 0.
In certain embodiments of Formula I, m is 0.
In certain embodiments of Formula I, m is 1.
In certain embodiments of Formula I, Y is (CH(R$^5$))$_n$ and n is 1.
In certain embodiments of Formula I, R$^5$ is H.
In certain embodiments of Formula I, R$^5$ is methyl.
In certain embodiments of Formula I, R$^4$ is N(R$^{4'}$)(R$^{4''}$) and R$^{4'}$ is H.
In certain embodiments of Formula I, R$^4$ is N(R$^{4'}$)(R$^{4''}$) and R$^{4''}$ is H.
In certain embodiments of Formula I, R$^{4''}$ is H.
In certain embodiments of Formula I, R$^{4''}$ is lower alkyl.
In certain embodiments of Formula I, R$^{4''}$ is lower alkyl.
In certain embodiments of Formula I, q is 0.
In certain embodiments of Formula I, q is 1.

In certain embodiments of Formula I, R$^3$ is halogen.
In certain embodiments of Formula I, R$^3$ is lower alkoxy or lower haloalkyl.

The application further provides a compound of Formula II

II or a pharmaceutically acceptable salt thereof,
wherein:
X is CH$_2$ or CH(R$^{1'}$);
Y$^1$ is CH$_2$ or C(O); and
Y$^2$ is CH$_2$, CH(R$^{1'}$), NH, N(R$^{1'}$), or O; and
   R$^{1'}$ is lower alkyl.

In certain embodiments of Formula II, X is CH$_2$.
In certain embodiments of Formula II, Y$^1$ is CH$_2$.
In certain embodiments of Formula II, Y$^2$ is CH(R$^{1'}$) and R$^{1'}$ is methyl.
In certain embodiments of Formula II, Y$^2$ is CH$_2$.
In certain embodiments of Formula II, Y$^2$ is N(R$^{1'}$) and R$^{1'}$ is methyl.
In certain embodiments of Formula II, Y$^2$ is NH.
In certain embodiments of Formula II, Y$^2$ is O.
In certain embodiments of Formula II, X is CH$_2$, Y$^1$ is C(O), and Y$^2$ is NH.
In certain embodiments of Formula II, X is CH(R$^{1'}$).

The application further provides a compound of Formula III

III or a pharmaceutically acceptable salt thereof,
wherein:
X is CH$_2$ or CH(R$^{1'}$);
Y$^1$ and Y$^3$ are each independently NH or O;
Y$^2$ is CH$_2$ or CH(R$^{1'}$); and
   R$^{1'}$ is lower alkyl.

In certain embodiments of Formula III, Y$^1$ is O.
In certain embodiments of Formula III, Y$^3$ is NH.
In certain embodiments of Formula III, Y$^2$ is CH$_2$.
In certain embodiments of Formula III, Y$^2$ is CH(R$^{1'}$) and R$^{1'}$ is methyl.

The application further provides a compound of Formula IV:

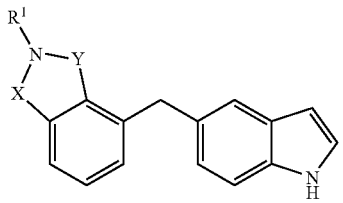

or a pharmaceutically acceptable salt thereof,
wherein:
X is $(CH_2)_m$;
  m is 1 or 2;
Y is $(CH_2)_n$;
  n is 1 or 2; and
$R^1$ is H or lower alkyl.

The application further provides a compound of Formula V:

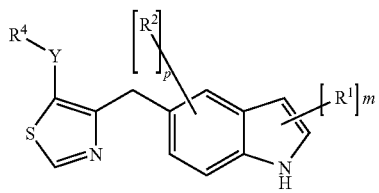

or a pharmaceutically acceptable salt thereof,
wherein:
Y is $(CH(R^5))_n$;
  n is 0, 1, or 2;
$R^1$ and $R^2$ are each independently CN, $C(O)N(R^{1'})_2$, $S(O)_2R^{1'}$, halogen, lower alkyl, lower haloalkyl, or lower alkoxy;
  $R^{1'}$ is H or lower alkyl;
m is 0 or 1;
p is 0, 1, or 2;
$R^4$ is $N(R^{4'})(R^{4''})$;
  $R^{4'}$ and $R^{4''}$ are each independently H, lower alkyl, lower hydroxyalkyl, lower alkoxyalkyl, lower cycloalkyl, lower haloalkyl, or $R^{4'}$ and $R^{4''}$ together form lower heteroaryl or lower heterocycloalkyl, optionally substituted with lower alkyl, hydroxy, lower alkoxy, lower haloalkyl, or oxo; and
each $R^5$ is independently H, lower alkyl, lower alkoxy, lower hydroxyalkyl, or lower haloalkyl.

The application further provides a compound of Formula VI:

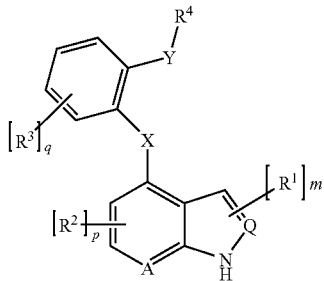

or a pharmaceutically acceptable salt thereof,
wherein:
X is $CH_2$, CH(OH), or C(O);
Y is $(CH(R^5))_n$, $O(CH(R^5))_n$, or C(O);
  n is 0, 1, or 2;
Q is CH, $C(R^1)$, or N;
A is CH, $C(R^2)$, or N;
$R^1$ and $R^2$ are each independently CN, $C(O)NH_2$, $S(O)_2R^{1'}$, halogen, lower alkyl, lower haloalkyl, or lower alkoxy;
  $R^{1'}$ is lower alkyl;
m is 0 or 1;
p is 0, 1, or 2;
$R^3$ is lower alkyl, lower alkoxy, lower haloalkyl, halogen, CN, $C(O)N(R^{1'})_2$, $NHS(O)_2R^{1'}$, or $N(R^{3'})(R^{3''})$;
  $R^{3'}$ and $R^{3''}$ are each independently H, lower alkyl, lower haloalkyl, or $R^{3'}$ and $R^{3''}$ together form lower heteroaryl or lower heterocycloalkyl, optionally substituted with lower alkyl, hydroxy, lower alkoxy, lower haloalkyl, or oxo;
q is 0, 1, or 2;
$R^4$ is $N(R^{4'})(R^{4''})$;
  $R^{4'}$ and $R^{4''}$ are each independently H, lower alkyl, lower hydroxyalkyl, lower alkoxyalkyl, lower cycloalkyl, lower haloalkyl, or $R^{4'}$ and $R^{4''}$ together form lower heteroaryl or lower heterocycloalkyl, optionally substituted with lower alkyl, hydroxy, lower alkoxy, lower haloalkyl, or oxo; and
each $R^5$ is independently H, lower alkyl, lower alkoxy, lower hydroxyalkyl, or lower haloalkyl.

The application further provides a compound of Formula VII:

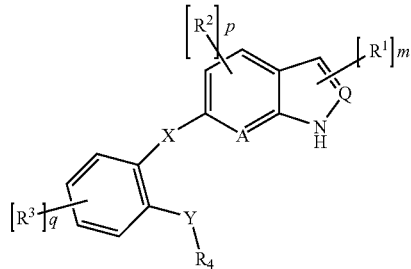

or a pharmaceutically acceptable salt thereof,
wherein:
X is $CH_2$, CH(OH), or C(O);
Y is $(CH(R^5))_n$, $O(CH(R^5))_n$, or C(O);
  n is 0, 1, or 2;
Q is CH, $C(R^1)$, or N;
A is CH, $C(R^2)$, or N;
$R^1$ and $R^2$ are each independently CN, $C(O)NH_2$, $S(O)_2R^{1'}$, halogen, lower alkyl, lower haloalkyl, or lower alkoxy;
  $R^{1'}$ is lower alkyl;
m is 0 or 1;
p is 0, 1, or 2;
$R^3$ is lower alkyl, lower alkoxy, lower haloalkyl, halogen, CN, $C(O)N(R^{1'})_2$, $NHS(O)_2R^{1'}$, or $N(R^{3'})(R^{3''})$;
  $R^{3'}$ and $R^{3''}$ are each independently H, lower alkyl, lower haloalkyl, or $R^{3'}$ and $R^{3''}$ together form lower heteroaryl or lower heterocycloalkyl, optionally substituted with lower alkyl, hydroxy, lower alkoxy, lower haloalkyl, or oxo;
q is 0, 1, or 2;
$R^4$ is $N(R^{4'})(R^{4''})$;
  $R^{4'}$ and $R^{4''}$ are each independently H, lower alkyl, lower hydroxyalkyl, lower alkoxyalkyl, lower cycloalkyl, lower haloalkyl, or $R^{4'}$ and $R^{4''}$ together form lower heteroaryl or lower heterocycloalkyl, optionally substituted with lower alkyl, hydroxy, lower alkoxy, lower haloalkyl, or oxo; and each R⁵ is independently H, lower alkyl, lower alkoxy, lower hydroxyalkyl, or lower haloalkyl.

The application further provides a compound selected from the group consisting of:
[2-(1H-Indol-5-ylmethyl)-benzyl]-methyl-amine;
8-(1H-Indol-5-ylmethyl)-1,2,3,4-tetrahydro-isoquinoline;
5-(1H-Indol-5-ylmethyl)-1,2,3,4-tetrahydro-isoquinoline;
1-[2-(1H-Indol-5-ylmethyl)-phenyl]-ethylamine;
{(R)-1-[2-(1H-Indol-5-ylmethyl)-phenyl]-ethyl}-methyl-amine;
{(S)-1-[2-(1H-Indol-5-ylmethyl)-phenyl]-ethyl}-methyl-amine;
[2-(1H-Indol-5-ylmethyl)-3-methoxy-benzyl]-methyl-amine;
[3-Fluoro-2-(1H-indol-5-ylmethyl)-benzyl]-methyl-amine;
[2-(7-Fluoro-1H-indol-5-ylmethyl)-benzyl]-methyl-amine;
[2-(1H-Indol-5-ylmethyl)-6-methoxy-benzyl]-methyl-amine;
8-(1H-Indol-5-ylmethyl)-2-methyl-1,2,3,4-tetrahydro-isoquinoline;
[2-(1H-Indol-5-ylmethyl)-3-trifluoromethyl-benzyl]-methyl-amine;
[2-(1H-Indazol-5-ylmethyl)-benzyl]-methyl-amine;
2-(1H-Indol-5-ylmethyl)-phenylamine;
[2-(1H-Indol-6-ylmethyl)-benzyl]-methyl-amine;
[2-(1H-Indol-4-ylmethyl)-benzyl]-methyl-amine;
[2-(1H-Indol-5-ylmethyl)-benzyl]-dimethyl-amine;
5-(2-Azetidin-1-ylmethyl-benzyl)-1H-indole;
Ethyl-[2-(1H-indol-5-ylmethyl)-benzyl]-amine;
[5-Fluoro-2-(1H-indol-5-ylmethyl)-benzyl]-methyl-amine;
2-[2-(1H-Indol-5-ylmethyl)-benzylamino]-ethanol;
Cyclopropyl-[2-(1H-indol-5-ylmethyl)-benzyl]-amine;
2-(1H-Indol-5-ylmethyl)-benzylamine;
(1H-Indol-5-yl)-(2-methylaminomethyl-phenyl)-methanol;
5-(2-Imidazol-1-ylmethyl-benzyl)-1H-indole;
5-(2-Piperazin-1-yl-benzyl)-1H-indole;
[5-Chloro-2-(1H-indol-5-ylmethyl)-benzyl]-methyl-amine;
{2-[2-(1H-Indol-5-ylmethyl)-phenyl]-ethyl}-methyl-amine;
5-(2-Methylaminomethyl-benzyl)-1H-indole-3-carbonitrile;
5-(2-Methylaminomethyl-benzyl)-1H-indole-3-carboxylic acid amide;
Methyl-[2-(1H-pyrrolo[2,3-b]pyridin-5-ylmethyl)-benzyl]-amine;
[3-(1H-Indol-5-ylmethyl)-benzyl]-methyl-amine;
[2-(1H-Indol-5-ylmethyl)-4-methoxy-benzyl]-methyl-amine;
[2-(1H-Indol-5-ylmethyl)-5-methoxy-benzyl]-methyl-amine;
[2-(1H-Indol-5-ylmethyl)-benzyl]-(2,2,2-trifluoro-ethyl)-amine;
5-(2-Methylaminomethyl-benzyl)-1H-indole-2-carbonitrile;
(2-Dimethylaminomethyl-phenyl)-(1H-indol-5-yl)-methanone;
4-(1H-Indol-5-ylmethyl)-3-methylaminomethyl-benzonitrile;
[2-(1H-Indol-5-ylmethyl)-5-morpholin-4-yl-benzyl]-methyl-amine;
5-(2-Methylaminomethyl-benzyl)-1H-indole-2-carboxylic acid amide;
N-[4-(1H-Indol-5-ylmethyl)-3-methylaminomethyl-phenyl]-methanesulfonamide;
1-[2-(1H-Indol-5-ylmethyl)-phenyl]-piperazin-2-one;
3-(1H-Indol-5-ylmethyl)-4-methylaminomethyl-benzonitrile;
3-(1H-Indol-5-ylmethyl)-4-methylaminomethyl-benzamide;
[4-(1H-Indol-5-ylmethyl)-thiazol-5-ylmethyl]-methyl-amine;
2-[2-(1H-Indol-5-ylmethyl)-phenoxy]-ethylamine;
2-Amino-1-[2-(1H-indol-5-ylmethyl)-phenyl]-ethanol;
5-(2-Morpholin-4-yl-benzyl)-1H-indole;
[2-(2-Methanesulfonyl-1H-indol-5-ylmethyl)-benzyl]-methyl-amine; and
5-(2-Morpholin-2-yl-benzyl)-1H-indole.

In one aspect, the application provides a pharmaceutical composition comprising any one of the compounds described herein and a pharmaceutically acceptable carrier.

In one aspect, the application provides a method for treating diseases associated with monoamine reuptake inhibitors, comprising administering to a subject in need thereof a pharmaceutically effective amount of any one of the compounds described herein.

In one aspect, the application provides a method for treating anxiety, depression, or both, said method comprising administering to a subject in need thereof a pharmaceutically effective amount of any one of the compounds described herein.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms.

"Lower alkyl" refers to a linear or branched alkyl group of one to six carbon atoms, i.e. $C_1$-$C_6$alkyl. Examples of lower alkyl groups include, but are not limited to, methyl, ethyl, propyl, isopropyl, isobutyl, sec butyl, tert butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Lower alkoxy" means a moiety of the formula —OR, wherein R is a lower alkyl moiety as defined herein. Examples of lower alkoxy moieties include, but are not limited to, methoxy, ethoxy, isopropoxy, tert-butoxy and the like.

"Lower alkoxyalkyl" means a moiety of the formula —R'—R", where R' is alkylene and R" is lower alkoxy as defined herein. Exemplary lower alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylsulfonyl" means a moiety of the formula —$SO_2$—R' where R' is alkyl as defined herein.

"Amino" means a moiety of the formula —NRR' wherein R and R' each independently is hydrogen or alkyl as defined herein. Amino thus includes "alkylamino" (where one of R and R' is alkyl and the other is hydrogen) and "dialkylamino" (where R and R' are both alkyl.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, azulenyl, oxydiphenyl, biphenyl, methylenediphenyl, aminodiphenyl, diphenylsulfidyl, diphenylsulfonyl, diphenylisopropylidenyl, benzodioxanyl, benzodioxylyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like. Preferred aryl include optionally substituted phenyl and optionally substituted naphthyl.

"Lower cycloalkyl" means a monovalent saturated carbocyclic moiety consisting of mono- or bicyclic rings of 3 to 7 ring carbon atoms, preferably 3 to 6 carbon atoms. Lower cycloalkyl can optionally be substituted with one or more substituents, wherein each substituent is independently hydroxy, alkyl, lower alkoxy, halo, lower haloalkyl, amino, monoalkylamino, or dialkylamino, unless otherwise specifically indicated. Examples of lower cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" or "cycloalkyl alkyl" means a moiety of the formula —R'—R", where R' is alkylene and R" is lower cycloalkyl as defined herein.

"Heteroalkyl" means an alkyl radical as defined herein, including a branched $C_4$-$C_7$-alkyl, wherein one, two or three hydrogen atoms have been replaced with a substituent independently selected from the group consisting of $OR^a$, $NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, lower cycloalkyl, or cycloalkylalkyl; $R^b$ and $R^c$ are independently of each other hydrogen, acyl, alkyl, lower cycloalkyl, or cycloalkylalkyl; and when n is 0, $R^d$ is hydrogen, alkyl, lower cycloalkyl, or cycloalkylalkyl, and when n is 1 or 2, $R^d$ is alkyl, lower cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Lower heteroaryl" means a monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the lower heteroaryl radical will be on an aromatic ring. The lower heteroaryl ring may be optionally substituted as defined herein. Examples of lower heteroaryl moieties include, but are not limited to, optionally substituted imidazolyl, oxazolyl, isoxazolyl, thiazolyl, isothiazolyl, oxadiazolyl, thiadiazolyl, pyrazinyl, pyridazinyl, thiophenyl, furanyl, pyranyl, pyridinyl, pyrrolyl, pyrazolyl, pyrimidyl, quinolinyl, isoquinolinyl, quinazolinyl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like.

The terms "halo" and "halogen", which may be used interchangeably, refer to a substituent fluoro, chloro, bromo, or iodo.

"Lower haloalkyl" means lower alkyl as defined herein in which one or more hydrogen has been replaced with same or different halogen. Exemplary lower haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a lower haloalkyl moiety as defined herein. Examples of haloalkoxy moieties include, but are not limited to, trifluoromethoxy, difluoromethoxy, 2,2,2-trifluoroethoxy, and the like.

"Lower hydroxyalkyl" refers to a subset of heteroalkyl and refers in particular to an lower alkyl moiety as defined herein that is substituted with one or more, preferably one, two or three hydroxy groups, provided that the same carbon atom does not carry more than one hydroxy group. Representative examples include, but are not limited to, hydroxymethyl, 2 hydroxyethyl, 2 hydroxypropyl, 3 hydroxypropyl, 1-(hydroxymethyl)-2-methylpropyl, 2 hydroxybutyl, 3 hydroxybutyl, 4 hydroxybutyl, 2,3 dihydroxypropyl, 2-hydroxy-1-hydroxymethylethyl, 2,3 dihydroxybutyl, 3,4 dihydroxybutyl and 2 (hydroxymethyl)-3 hydroxypropyl.

"Lower heterocycloalkyl" means a monovalent saturated moiety, consisting of one to three rings, incorporating one, two, three, or four heteroatoms (chosen from nitrogen, oxygen or sulfur). The lower heterocycloalkyl ring may be optionally substituted as defined herein. Examples of lower heterocycloalkyl moieties include, but are not limited to, optionally substituted piperidinyl, piperazinyl, homopiperazinyl, azepanyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, benzothiazolidinyl, benzoazolylidinyl, dihydrofuranyl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like. Preferred lower heterocycloalkyl include tetrahydropyranyl, tetrahydrofuranyl, piperidinyl, piperazinyl and pyrrolidinyl.

"Optionally substituted", when used in association with "aryl", "phenyl", "lower heteroaryl" (including indolyl such as indol-1-yl, indol-2-yl and indol-3-yl, 2,3-dihydroindolyl such as 2,3-dihydroindol-1-yl, 2,3-dihydroindol-2-yl and 2,3-dihydroindol-3-yl, indazolyl such as indazol-1-yl, indazol-2-yl and indazol-3-yl, benzimidazolyl such as benzimidazol-1-yl and benzimidazol-2-yl, benzothiophenyl such as benzothiophen-2-yl and benzothiophen-3-yl, benzoxazol-2-yl, benzothiazol-2-yl, thienyl, furanyl, pyridinyl, pyrimidinyl, pyridazinyl, pyrazinyl, oxazolyl, thiazolyl, isoxazolyl, isothiazolyl, imidazolyl, pyrazolyl and quinolinyl) or "lower heterocycloalkyl", means an aryl, phenyl, lower heteroaryl or lower heterocycloalkyl which is optionally substituted independently with one to four substituents, preferably one or two substituents selected from alkyl, lower cycloalkyl, lower alkoxy, halo, lower haloalkyl, haloalkoxy, cyano, nitro, heteroalkyl, amino, acylamino, mono-alkylamino, di-alkylamino, lower hydroxyalkyl, lower alkoxyalkyl, benzyloxy, cycloalkylalkyl, cycloalkoxy, cycloalkylalkoxy, alkylsulfonyloxy, optionally substituted thiophenyl, optionally substituted pyrazolyl, optionally substituted pyridinyl, morpholinocarbonyl, —$(CH_2)_q$—$S(O)_rR^f$; —$(CH_2)_q$—$NR^gR^h$;

—$(CH_2)_q$—C(=O)—$NR^gR^h$; —$(CH_2)_q$—C(=O)—C(=O)—$NR^gR^h$; —$(CH_2)_q$—$SO_2$—$NR^gR^h$; —$(CH_2)_q$—N($R^f$)—C(=O)—$R^i$; —$(CH_2)_q$—C(=O)—$R^i$; or —$(CH_2)_q$—N($R^f$)—$SO_2$—$R^g$; where q is 0 or 1, r is from 0 to 2, $R^f$, $R^g$, and $R^h$ each independently is hydrogen or alkyl, and each $R^1$ is independently hydrogen, alkyl, hydroxy, or lower alkoxy. Certain preferred optional substituents for "aryl", "phenyl", "lower heteroaryl" "lower cycloalkyl" or "lower heterocycloalkyl" include alkyl, halo, lower haloalkyl, lower alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like.

Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disease states" associated with serotonin, norepinephrine and/or dopamine neurotransmission include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, haemorrhage, and disorders and disease states of the urinary tract. "Disease states" associated with serotonin, norepinephrine and/or dopamine neurotransmission also include inflammation conditions in a subject. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions.

"Depression" as used herein includes, but is not limited to, major depression, long-term depression, treatment resistant depression, dysthymia, mental states of depressed mood characterised by feelings of sadness, despair, discouragement, "blues", melancholy, feelings of low self esteem, guilt and self reproach, withdrawal from interpersonal contact, and somatic symptoms such as eating and sleep disturbances.

"Anxiety" as used herein includes, but is not limited to, unpleasant or undesirable emotional states associated with psychophysiological responses to anticipation of unreal, imagined or exaggerated danger or harm, and physical concomitants such as increased heart rate, altered respiration rate, sweating, trembling, weakness and fatigue, feelings of impending danger, powerlessness, apprehension and tension.

"Disorders of the urinary tract" or "uropathy" used interchangeably with "symptoms of the urinary tract" means the pathologic changes in the urinary tract. Examples of urinary tract disorders include, but are not limited to, stress incontinence, urge incontence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic hypersensitivity" includes, but is not limited to, pelvic pain, interstitial (cell) cystitis, prostatodynia, prostatitis, vulvadynia, urethritis, orchidalgia, overactive bladder, and the like.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28th Edition, W. B. Saunders Company, Philadelphia, Pa.). The goal of treatment of pain is to reduce the degree of severity of pain perceived by a treatment subject.

"Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v. 4.0, a Beilstein Institute computerized system for the generation of IUPAC systematic nomenclature. Chemical structures shown herein were prepared using ISIS® version 2.2. Any open valency appearing on a carbon, oxygen, sulfur or nitrogen atom in the structures herein indicates the presence of a hydrogen atom.

Whenever a chiral carbon is present in a chemical structure, it is intended that all stereoisomers associated with that chiral carbon are encompassed by the structure, so as to include specific enantiomers.

All patents and publications identified herein are incorporated herein by reference in their entirety.

Compounds of the Invention

Representative compounds in accordance with the methods of the invention are shown in Table I:

TABLE I

| # | Structure | Name | MS | MP |
|---|---|---|---|---|
| 1 | 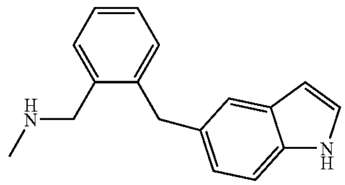 | [2-(1H-Indol-5-ylmethyl)-benzyl]-methyl-amine | 251 | 198-199 |
| 2 | 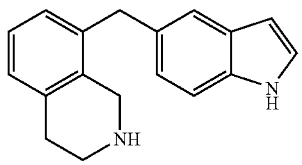 | 8-(1H-Indol-5-ylmethyl)-1,2,3,4-tetrahydro-isoquinoline | 263 | 173-174 |
| 3 | 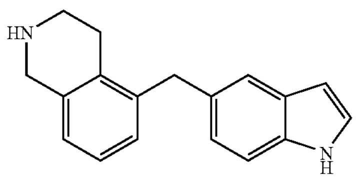 | 5-(1H-Indol-5-ylmethyl)-1,2,3,4-tetrahydro-isoquinoline | 263 | 194-195 |
| 4 | 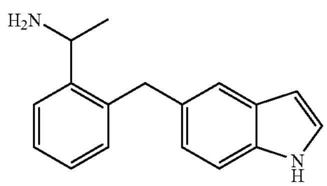 | 1-[2-(1H-Indol-5-ylmethyl)-phenyl]-ethylamine | 251 | |
| 5 | 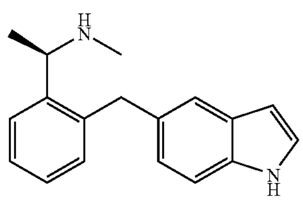 | {(R)-1-[2-(1H-Indol-5-ylmethyl)-phenyl]-ethyl}-methyl-amine | 265 | |
| 6 | 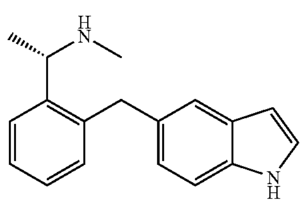 | {(S)-1-[2-(1H-Indol-5-ylmethyl)-phenyl]-ethyl}-methyl-amine | 265 | |
| 7 | 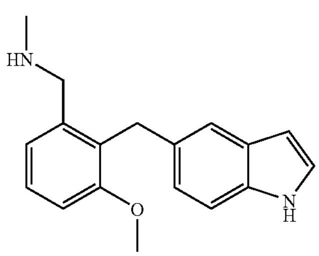 | [2-(1H-Indol-5-ylmethyl)-3-methoxy-benzyl]-methyl-amine | 281 | |

TABLE I-continued

| # | Structure | Name | MS | MP |
|---|---|---|---|---|
| 8 | 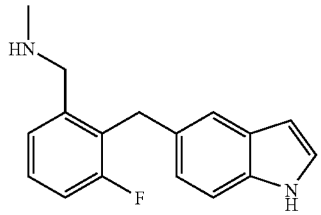 | [3-Fluoro-2-(1H-indol-5-ylmethyl)-benzyl]-methyl-amine | 269 | |
| 9 | 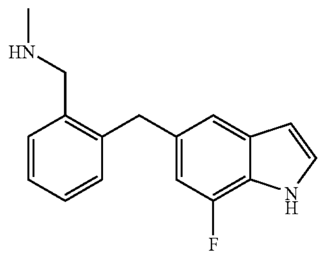 | [2-(7-Fluoro-1H-indol-5-ylmethyl)-benzyl]-methyl-amine | 269 | |
| 10 | 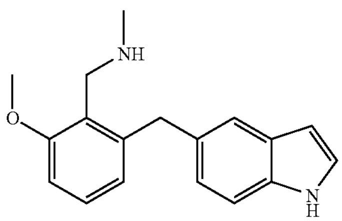 | [2-(1H-Indol-5-ylmethyl)-6-methoxy-benzyl]-methyl-amine | 281 | |
| 11 | 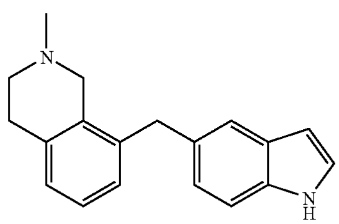 | 8-(1H-Indol-5-ylmethyl)-2-methyl-1,2,3,4-tetrahydro-isoquinoline | 277 | |
| 12 | 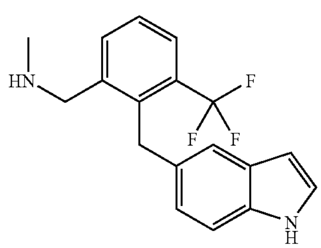 | [2-(1H-Indol-5-ylmethyl)-3-trifluoromethyl-benzyl]-methyl-amine | 319 | |
| 13 | 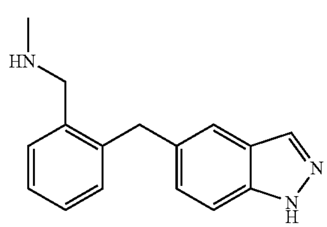 | [2-(1H-Indazol-5-ylmethyl)-benzyl]-methyl-amine | 252 | |
| 14 | 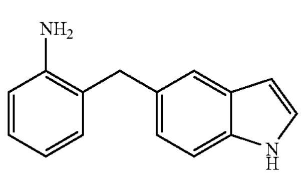 | 2-(1H-Indol-5-ylmethyl)-phenylamine | 223 | |

TABLE I-continued

| # | Name | MS | MP |
|---|------|-----|-----|
| 15 | [2-(1H-Indol-6-ylmethyl)-benzyl]-methyl-amine | 251 | 132 |
| 16 | [2-(1H-Indol-4-ylmethyl)-benzyl]-methyl-amine | 251 | 111-12 |
| 17 | [2-(1H-Indazol-5-ylmethyl)-benzyl]-dimethyl-amine | 265 | |
| 18 | 5-(2-Azetidin-1-ylmethyl-benzyl)-1H-indole | 277 | 128-130 |
| 19 | Ethyl-[2-(1H-indol-5-ylmethyl)-benzyl]-amine | 265 | |
| 20 | [5-Fluoro-2-(1H-indol-5-ylmethyl)-benzyl]-methyl-amine | 269 | 162-163 |
| 21 | 2-[2-(1H-Indol-5-ylmethyl)-benzylamino]-ethanol | 281 | 117-118 |

TABLE I-continued
| # | Structure | Name | MS | MP |
|---|---|---|---|---|
| 22 | 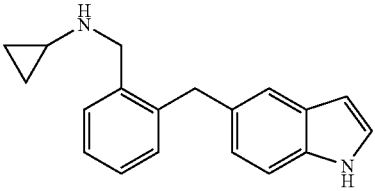 | Cyclopropyl-[2-(1H-indol-5-ylmethyl)-benzyl]-amine | 277 | |
| 23 | 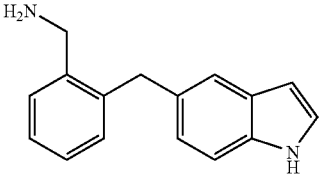 | 2-(1H-Indol-5-ylmethyl)-benzylamine | 237 | |
| 24 | 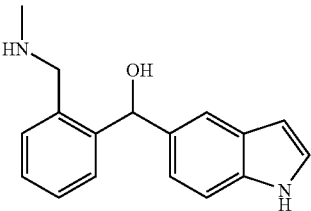 | (1H-Indol-5-yl)-(2-methylaminomethyl-phenyl)-methanol | 266 | 75-78 |
| 25 | 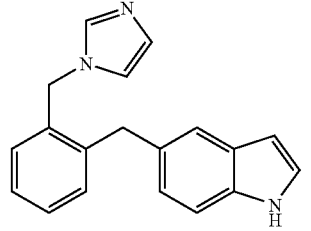 | 5-(2-Imidazol-1-ylmethyl-benzyl)-1H-indole | 288 | 61-67 |
| 26 | 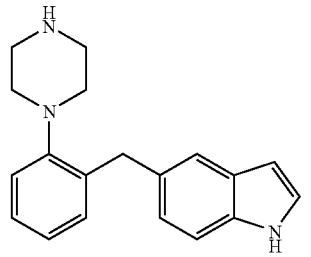 | 5-(2-Piperazin-1-yl-benzyl)-1H-indole | 292 | |
| 27 | 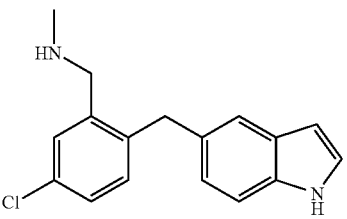 | [5-Chloro-2-(1H-indol-5-ylmethyl)-benzyl]-methyl-amine | 285 | 164-165 |
| 28 | 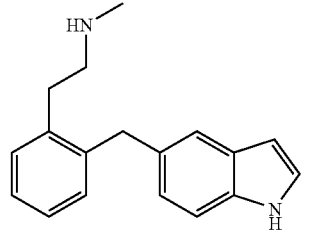 | {2-[2-(1H-Indol-5-ylmethyl)-phenyl]-ethyl}-methyl-amine | 265 | 95-97 |

TABLE I-continued

| # | Structure | Name | MS | MP |
|---|---|---|---|---|
| 29 | 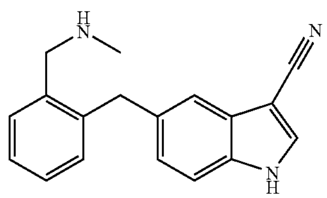 | 5-(2-Methylaminomethyl-benzyl)-1H-indole-3-carbonitrile | 276 | 179-180 |
| 30 | 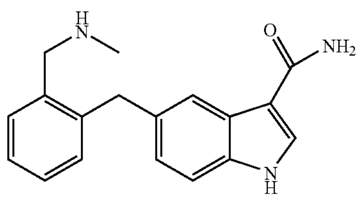 | 5-(2-Methylaminomethyl-benzyl)-1H-indole-3-carboxylic acid amide | 294 | |
| 31 | 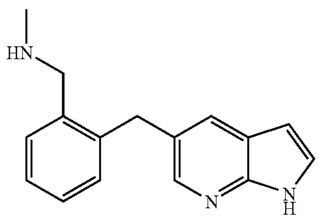 | Methyl-[2-(1H-pyrrolo[2,3-b]pyridin-5-ylmethyl)-benzyl]-amine | 252 | |
| 32 | 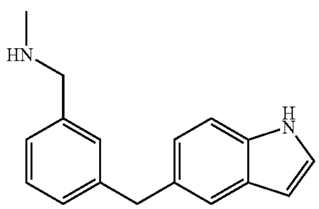 | [3-(1H-Indol-5-ylmethyl)-benzyl]-methyl-amine | 251 | 153 |
| 33 | 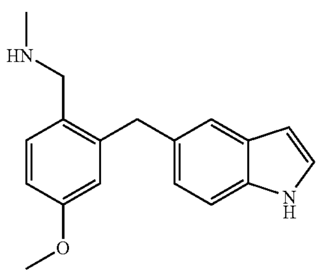 | [2-(1H-Indol-5-ylmethyl)-4-methoxy-benzyl]-methyl-amine | 281 | 157-158 |
| 34 | 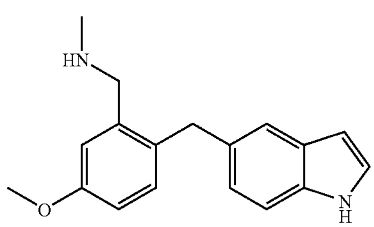 | [2-(1H-Indol-5-ylmethyl)-5-methoxy-benzyl]-methyl-amine | 281 | 155-156 |
| 35 | 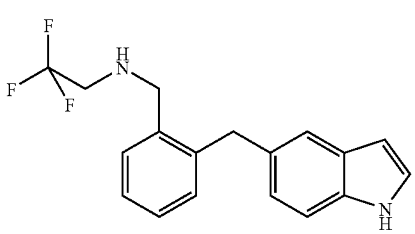 | [2-(1H-Indol-5-ylmethyl)-benzyl]-(2,2,2-trifluoro-ethyl)-amine | 319 | |

TABLE I-continued

| # | Structure | Name | MS | MP |
|---|---|---|---|---|
| 36 | 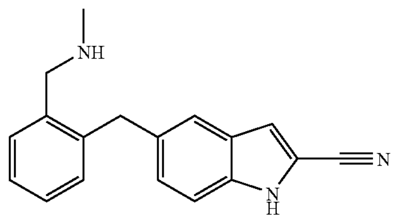 | 5-(2-Methylaminomethyl-benzyl)-1H-indole-2-carbonitrile | 276 | |
| 37 | 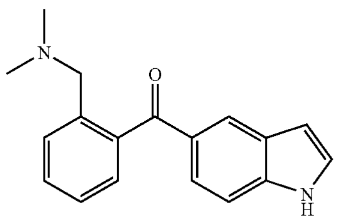 | (2-Dimethylaminomethyl-phenyl)-(1H-indol-5-yl)-methanone | 279 | |
| 38 | 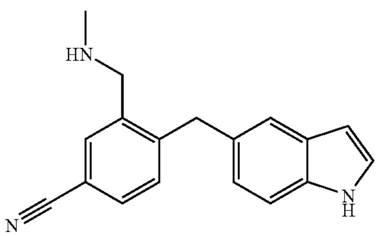 | 4-(1H-Indol-5-ylmethyl)-3-methylaminomethyl-benzonitrile | 276 | 144-145 |
| 39 | 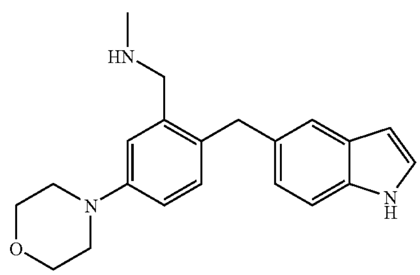 | [2-(1H-Indol-5-ylmethyl)-5-morpholin-4-yl-benzyl]-methyl-amine | 336 | 135-136 |
| 40 | 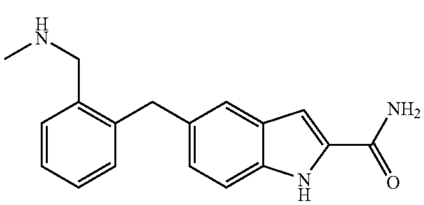 | 5-(2-Methylaminomethyl-benzyl)-1H-indole-2-carboxylic acid amide | 294 | |
| 41 | 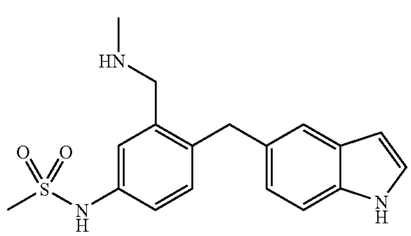 | N-[4-(1H-Indol-5-ylmethyl)-3-methylaminomethyl-phenyl]-methanesulfonamide | 344 | 125-126 |

TABLE I-continued

| # | Structure | Name | MS | MP |
|---|---|---|---|---|
| 42 | 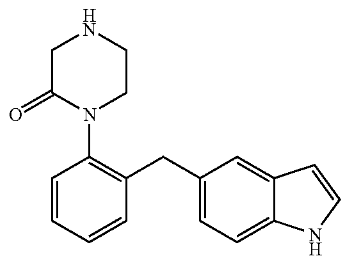 | 1-[2-(1H-Indol-5-ylmethyl)-phenyl]-piperazin-2-one | 306 | 100-102 |
| 43 | 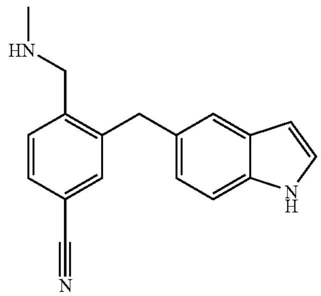 | 3-(1H-Indol-5-ylmethyl)-4-methylaminomethyl-benzonitrile | 276 | 160-163 |
| 44 | 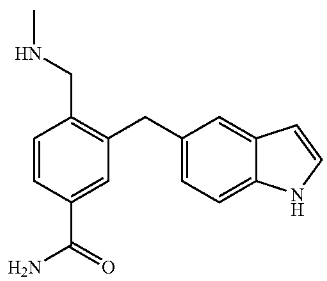 | 3-(1H-Indol-5-ylmethyl)-4-methylaminomethyl-benzamide | 294 | 97-100 |
| 45 | 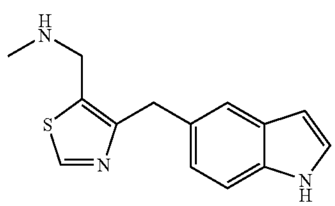 | [4-(1H-Indol-5-ylmethyl)-thiazol-5-ylmethyl]-methyl-amine | 258 | 152-153 |
| 46 | 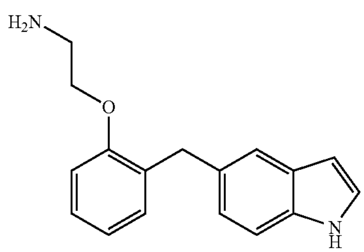 | 2-[2-(1H-Indol-5-ylmethyl)-phenoxy]-ethylamine | 267 | |
| 47 | 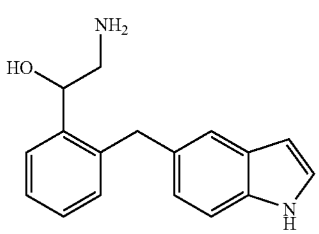 | 2-Amino-1-[2-(1H-indol-5-ylmethyl)-phenyl]-ethanol | 267 | 70-72 |

TABLE I-continued

| # | Structure | Name | MS | MP |
|---|---|---|---|---|
| 48 | 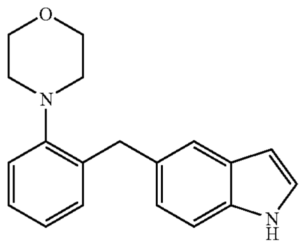 | 5-(2-Morpholin-4-yl-benzyl)-1H-indole | 293 | 189-190 |
| 49 | 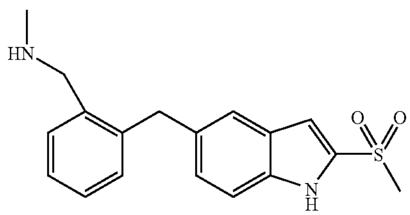 | [2-(2-Methanesulfonyl-1H-indol-5-ylmethyl)-benzyl]-methyl-amine | 329 | 179-180 |
| 50 | 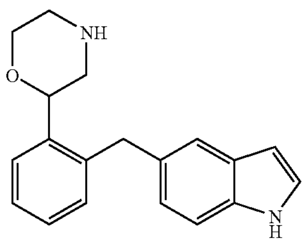 | 5-(2-Morpholin-2-yl-benzyl)-1H-indole | 293 | |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Utility

The compounds of the invention are usable for the treatment of diseases or conditions associated with serotonin neurotransmission, norepinephrine neuortransmission and/or dopamine neurotransmission. Such diseases and conditions include depressive and anxiolytic disorders, as well as schizophrenia and other psychoses, dyskinesias, drug addition, cognitive disorders, Alzheimer's disease, attention deficit disorders such as ADHD, obsessive-compulsive behaviour, panic attacks, social phobias, eating disorders such as obesity, anorexia, bulimia and "binge-eating", stress, hyperglycaemia, hyperlipidaemia, non-insulin-dependent diabetes, seizure disorders such as epilepsy, and treatment of conditions associated with neurological damage resulting from stroke, brain trauma, cerebral ischaemia, head injury, and haemorrhage.

The compounds of the invention are also usable for treatment of disorders and disease states of the urinary tract such as stress incontinence, urge incontinence, benign prostatic hypertrophy (BPH), prostatitis, detrusor hyperreflexia, outlet obstruction, urinary frequency, nocturia, urinary urgency, overactive bladder, pelvic hypersensitivity, urethritis, prostatodynia, cystitis, idiophatic bladder hypersensitivity.

The compounds of the invention also possess anti-inflammatory and/or analgesic properties in vivo, and accordingly, are expected to find utility in the treatment of disease states associated with pain conditions from a wide variety of causes, including, but not limited to, neuropathic pain, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Compounds of the invention are also useful for treatment of arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa. Representative pharmaceutical formulations containing a compound of the present invention are described below.

EXAMPLES

The following preparations and examples are given to those skilled in the art to more clearly understand and to practice the present invention. They should not be considered as limiting the scope of the invention, but merely as being illustrative and representative thereof.

Whenever a chiral carbon is present in a chemical structure, it is intended that all stereoisomers associated with that chiral carbon are encompassed by the structure, so as to include specific enantiomers.

The following abbreviations may be used in the Examples.

Abbreviations

ACE-Cl □-Chloroethyl chloroformate
AcOH Acetic acid
Bn Benzyl
(BOC)$_2$O Di-tert-butyl dicarbonate
t-BuLi tert-Butyllithium
t-BuOH tert-Butyl alcohol
m-CPBA 3-Chloroperoxybenzoic acid
DCE 1,2-Dichloroethane
DCM Dichloromethane/methylene chloride
DEA Diethylamine
DIPEA Diisopropylethylamine
DIBALH Diisobutylaluminum hydride
DMAP 4-Dimethylaminopyridine
DMF N,N-Dimethylformamide
DMP Dess Martin Periodinane (acetic acid 1,1-diacetoxy-3-oxo-1lambda*5*-ioda-2-oxa-indan-1-yl ester)
DMSO Dimethyl sulphoxide
Dppf 1,1'-Bis(diphenylphosphino)ferrocene
EDC 1-(3-Dimethylaminopropyl)-3-ethylcarbodiimide hydrochloride
EtOAc Ethyl acetate
HPLC High pressure liquid chromatography
HOBt 1-Hydroxybenzotriazole
LAH Lithium aluminum hydride
LHMDS Lithium bis(trimethylsilyl)amide
MeOH Methanol
MsCl Methanesulfonyl chloride
NMP 1-Methyl-2-pyrrolidinone
NBS N-Bromosuccinimide
PFBSF Perfluorobutanesulfonyl fluoride
PPTS Pyridinium p-toluenesulfonate
TBAF Tetrabutylammonium fluoride
TBAHS Tetrabutyl ammonium hydrogen sulfate
TBDMS tert-Butyldimethylsilyl
TMSI Iodotrimethylsilane
TEA Triethylamine
TIPS Triisopropylsilyl
TFA Trifluoroacetic acid
THF Tetrahydrofuran
TLC Thin layer chromatography
TMAF Tetramethylammonium fluoride
TMS Trimethylsilyl
p-TsOH p-Toluenesulfonic acid

Example 1

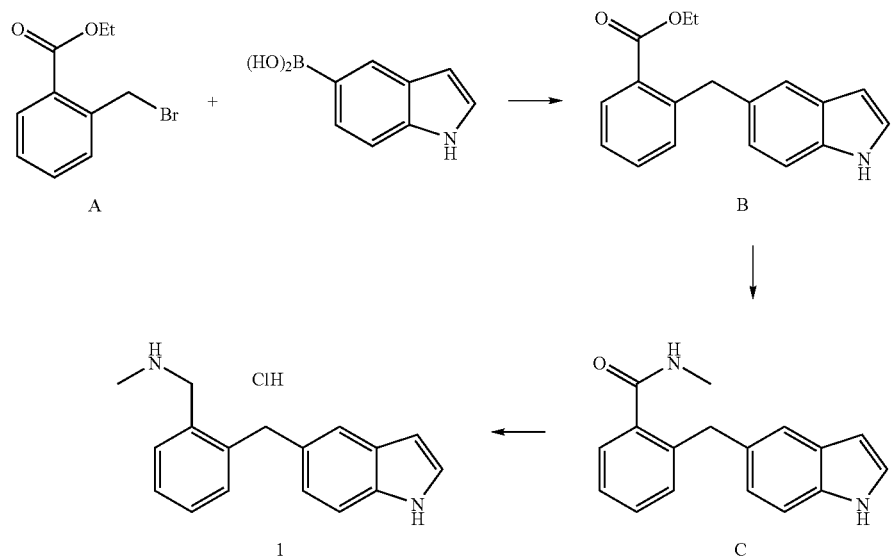

Preparation of intermediate A: Ethyl 2-methylbenzoate (15.0 g, 91 mmol) in ethyl acetate (400 mL) was treated with N-bromosuccinimide (19.5 g, 110 mmol). The resulting solution was illuminated with a 65 W mercury-halogen lamp for 16 h, which provided enough heat to bring the solution to a gentle reflux. The reaction mixture was cooled to room temperature, and ethyl acetate and water were added (100 mL each). After separation of the organic layer, the aqueous layer was extracted with ethyl acetate (400 mL). The combined organic extracts were washed twice with water (100 mL each) and then with brine (100 mL), and then dried over sodium sulfate, filtered, and concentrated under reduced pressure. The crude product so obtained was purified by flash chromatography (ethyl acetate/hexane) to afford A as a yellow oil (21.3 g).

Preparation of intermediate B: A mixture of A (6.9 g, 28 mmol), indole-5-boronic acid (7.3 g, 45 mmol), tetrakis(triphenylphosphine)palladium(0) (1.64 g, 1.5 mmol), and cesium fluoride (13.8 g, 91 mmol) in 1,2-dimethoxyethane (120 mL) was stirred at 85° C. for 44 h. The resulting dark brown suspension was filtered through Celite, and the solids were washed with diethyl ether. The crude product was adsorbed onto silica gel (20 g), and purified by flash chromatography (ethyl acetate/hexane) to afford B as a yellow oil (4.8 g).

Preparation of intermediate C: To a stirred suspension of methylamine hydrochloride (9.3 g, 138 mmol) in toluene (60 mL) at 0° C. was added a solution of trimethylaluminum in toluene (2M, 69 mL, 138 mmol) dropwise over 30 min. The resulting solution was stirred for 5 min at 0° C. followed by 2.5 h at room temperature, and then was added dropwise over 15 min to a solution of B (12.8 g, 46 mmol) in toluene (360 mL). The resulting mixture was stirred at 80° C. for 3 days, and was then cooled to 0° C. and treated carefully with aqueous hydrochloric acid (1M, 200 mL). The mixture was concentrated under reduced pressure to a volume of 200 mL, and extracted with ethyl acetate (700 mL, then 300 mL). The combined ethyl acetate extracts were washed with water and brine (100 mL each), dried over sodium sulfate, filtered and concentrated under reduced pressure. The crude residue so obtained was purified by flash chromatography (ethyl acetate/hexane) to afford C as a yellow solid (11.7 g).

Preparation of 1: To a solution of C (10.6 g, 40 mmol) in THF (300 mL) was added a solution of lithium aluminum hydride in THF (1M, 161 mL, 161 mmol) dropwise over 45 min. The mixture was stirred and heated to reflux for 40 h, then cooled to 0° C. and treated with crushed sodium sulfate decahydrate until no bubbling was noted. The resulting mixture was stirred at room temperature for 2 h and then filtered through Celite. The solids were washed with a mixture of dichloromethane and methanol. The combined filtrate was concentrated under reduced pressure, and the residue so obtained was partitioned between ethyl acetate (400 mL) and water (60 mL). The aqueous layer was extracted with additional ethyl acetate (400 mL), and combined organic extracts were washed with water and brine (60 mL each), dried over sodium sulfate, filtered, and concentrated under reduced pressure. The brown semisolid residue so obtained was purified by flash chromatography (methanol/dichloromethane/aqueous ammonium hydroxide) to afford the free base of 1 as a purple solid (7.34 g). A suspension of the free base of 1 (5.28 g, 20 mmol) in ethyl acetate (150 mL) and ethanol (0.5 mL) was heated to reflux, filtered hot, and cooled to 0° C. To that cooled solution was added a solution of hydrogen chloride in diethyl ether (1M, 42 mL, 42 mmol) dropwise over 30 min. The resulting suspension was stirred for 30 min at 0° C. and filtered. The solid was washed with cold diethyl ether and dried under vacuum to afford 1 as an off-white powder (5.75 g).

Similarly prepared compounds from Table I include: compounds 7, 8, 9, 10, 12, 13, 15, 16, 20, 27, 31, 32, 33, and 34.

Example 2

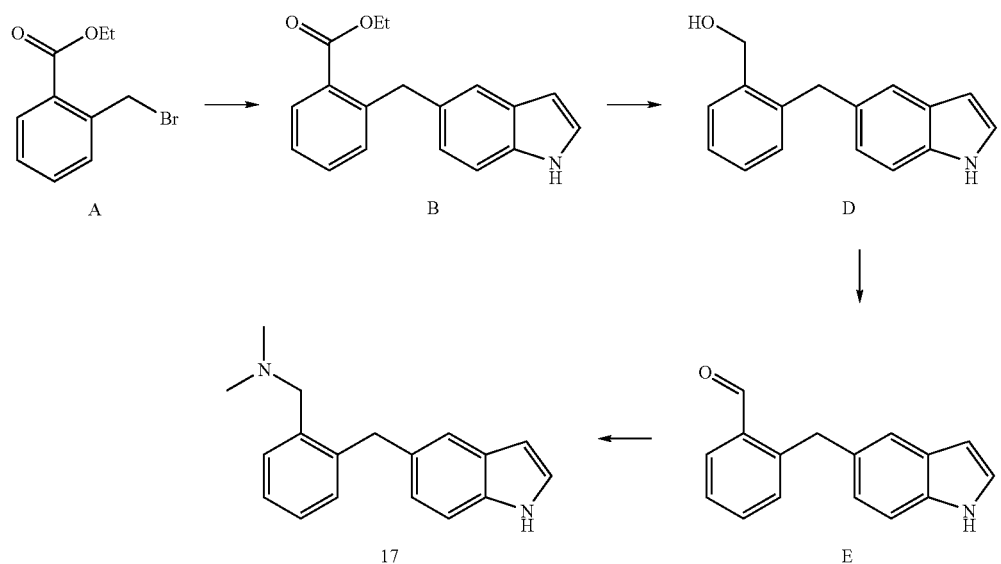

For preparation of intermediate B: See Example 1, above. Preparation of intermediate D: A solution of B (4.1 g, 15 mmol) in THF (100 mL) was cooled to 0° C., with stirring, whereupon a solution of lithium aluminum hydride in THF (1 M, 16 mL, 16 mmol) was added dropwise over 20 min. Stirring was continued for 2.5 h at 0° C., followed by the addition of pulverized sodium sulfate decahydrate. The resulting mixture was stirred at room temperature for 1 h and then filtered over diatomaceous earth. The filter cake was washed with methanol and dichloromethane, and the combined filtrates were concentrated under reduced pressure. The crude residue so obtained was partitioned between water and ethyl acetate, and the ethyl acetate layer was washed sequentially with water and brine, dried over sodium sulfate, filtered and concentrated under reduced pressure. The residue so obtained was purified by flash chromatography (ethyl acetate/hexane) to afford D as an off-white solid (3.0 g).

Preparation of intermediate E: To a solution of D (1.2 g, 5.16 mmol) in dichloromethane (48 mL) was added activated manganese (IV) oxide (6.2 g, 61 mmol). The resulting black suspension was stirred at reflux for 1.5 h, and was filtered while still hot through a glass microfiber filter. The filtrate was concentrated under reduced pressure, and the crude residue so obtained purified by flash chromatography (ethyl acetate/hexane) to afford E as a light brown solid (0.96 g).

Preparation of 17: To a solution of E (0.10 g, 0.43 mmol) and dimethylamine (0.51 mmol; from 0.26 mL of a 2.0 M solution in THF) was added sodium triacetoxyborohydride (0.13 g, 0.60 mmol). The mixture was stirred at room temperature for 4.5 h. A solution of saturated aqueous sodium bicarbonate (10 mL) was added, and the mixture was extracted with ethyl acetate. The ethyl acetate layer was washed sequentially with water and brine, dried over sodium sulfate, filtered and concentrated under reduced pressure. The light brown oil (0.12 g) so obtained was purified by flash chromatography (methanol/dichloromethane/aqueous ammonium hydroxide) to afford 17 as a light grey oil (0.10 g).

Similarly prepared compounds from Table I include: compounds 18, 19, 21, 22, 23, 35, 38, 43, 44, and 45.

Example 3

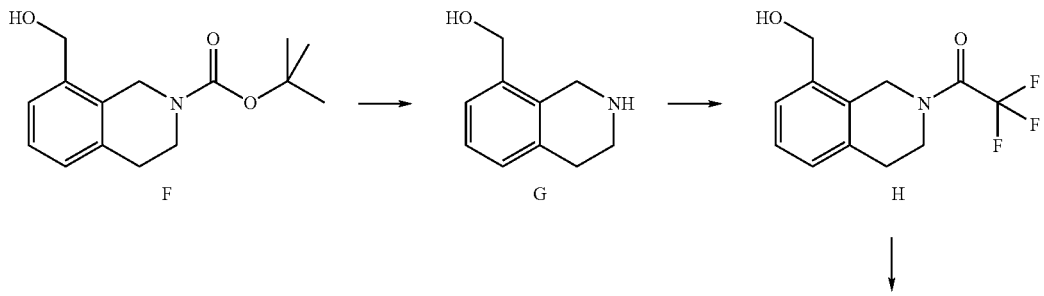

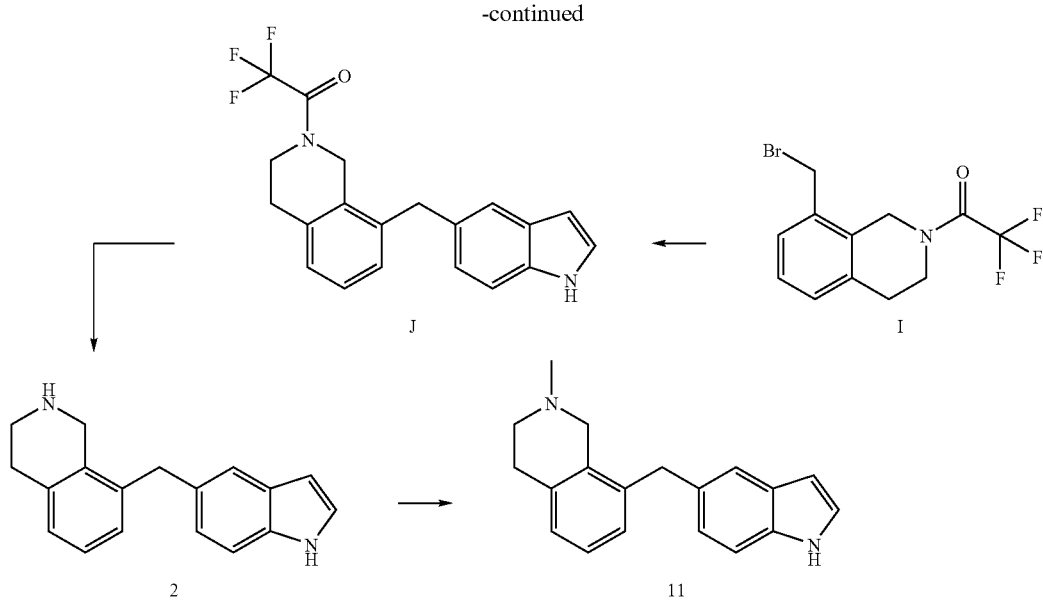

Preparation of intermediate F: To a stirred solution of 2-(tert-butoxycarbonyl)-1,2,3,4-tetrahydroisoquinoline-8-carboxylic acid (1.0 g, 3.6 mmol) in THF (20 mL) at 0° C., was added a solution of borane in THF (1.0 M, 7.2 mL, 7.2 mmol). The resulting solution was stirred for 20 min at 0° C., followed by 1 h at room temperature. Methanol was added, and the mixture was concentrated under reduced pressure. The residue so obtained was partitioned between ether and aqueous sodium hydroxide, and the ether layer was washed with brine, dried over sodium sulfate, filtered, and concentrated under reduced pressure. The crude residue so obtained was purified by flash chromatography (ethyl acetate/hexane) to afford F as a colorless oil which solidified on standing (0.98 g).

Preparation of intermediate G: To a solution of F (3.0 g, 11 mmol) in dichloromethane (10 mL) was added trifluoroacetic acid (9 mL), and the resulting mixture was stirred at room temperature for 2 h. The reaction mixture was made basic with 2.5 N aqueous sodium hydroxide, and extracted with dichloromethane. The combined extracts were washed with a small amount of brine, dried over sodium sulfate, filtered, and concentrated under reduced pressure. The crude residue so obtained purified by flash chromatography (methanol/dichloromethane/aqueous ammonium hydroxide) to afford G as a light yellow oil (2.5 g).

Preparation of intermediate H: To a solution of G (2.5 g, 15 mmol) in dichloromethane (50 mL) was added trifluoroacetic anhydride (7.0 g, 33 mmol) and pyridine (6.2 g, 45 mmol), and the mixture was stirred at room temperature for 1 h. The mixture was then washed in succession with 2 N aqueous hydrochloric acid, saturated aqueous sodium bicarbonate and brine. The organic phase was then dried over sodium sulfate, filtered, and concentrated under reduced pressure. The residue so obtained was dissolved in methanol, stirred with sodium carbonate (1.6 g, 15 mmol) for 1 h at room temperature, filtered, and concentrated under reduced pressure. The residue was partitioned between dichloromethane and 2 N aqueous hydrochloric acid, and the organic layer was washed with brine, dried over sodium sulfate, filtered and concentrated under reduced pressure to afford H as an oil (2.3 g) which was used in the next step without further purification.

Preparation of intermediate I: A mixture of H (2.3 g, 8.9 mmol), carbon tetrabromide (4.4 g, 13 mmol) and triphenylphosphine (3.5 g, 13 mmol) in dichloromethane (50 mL) were stirred at room temperature for 5 h. The reaction mixture was concentrated under reduced pressure, and the crude residue so obtained was purified by flash chromatography (ethyl acetate/hexane) to afford I as a white solid.

Preparation of intermediate J: A mixture of I (0.25 g, 0.78 mmol), indole-5-boronic acid (0.14 g, 0.85 mmol), tetrakis(triphenylphosphine)palladium(0) (0.04 g, 0.04 mmol), and cesium fluoride (0.35 g, 2.3 mmol) in 1,2-dimethoxyethane (10 mL) was stirred at reflux for 5 h. The resulting suspension was filtered, and the filtrate was partitioned between aqueous ammonium chloride and ethyl acetate. The organic layer was washed with brine, dried over sodium sulfate, filtered, and concentrated under reduced pressure, and the crude residue so obtained was purified by flash chromatography (ethyl acetate/hexane) to afford J as a yellow solid (0.17 g).

Preparation of 2: To a solution of J (0.17 g, 0.47 mmol) in methanol (10 mL) and water (0.6 mL) was added potassium carbonate (0.33 g, 2.4 mmol), and the resulting mixture was stirred at room temperature for 1 h, filtered, and concentrated under reduced pressure. The crude residue so obtained purified by flash chromatography (methanol/dichloromethane/aqueous ammonium hydroxide) to afford 2 as a white solid (0.10 g).

Preparation of 11: To a solution of 2 (0.050 g, 0.19 mmol) in 1,2-dichloroethane (2 mL) was added formaldehyde (0.04 mL of a 20% aqueous solution, 0.38 mmol) and sodium triacetoxyborohydride (0.080 g, 0.38 mmol), and the resulting mixture was stirred at room temperature for 1 h. Saturated aqueous sodium bicarbonate (1 mL) was added, and the mixture was filtered over diatomaceous earth and concentrated under reduced pressure. The crude residue so obtained purified by flash chromatography (methanol/dichloromethane/aqueous ammonium hydroxide) to afford 11 as a foam (0.040 g).

Similarly prepared compounds from Table I include compound 3.

Example 4

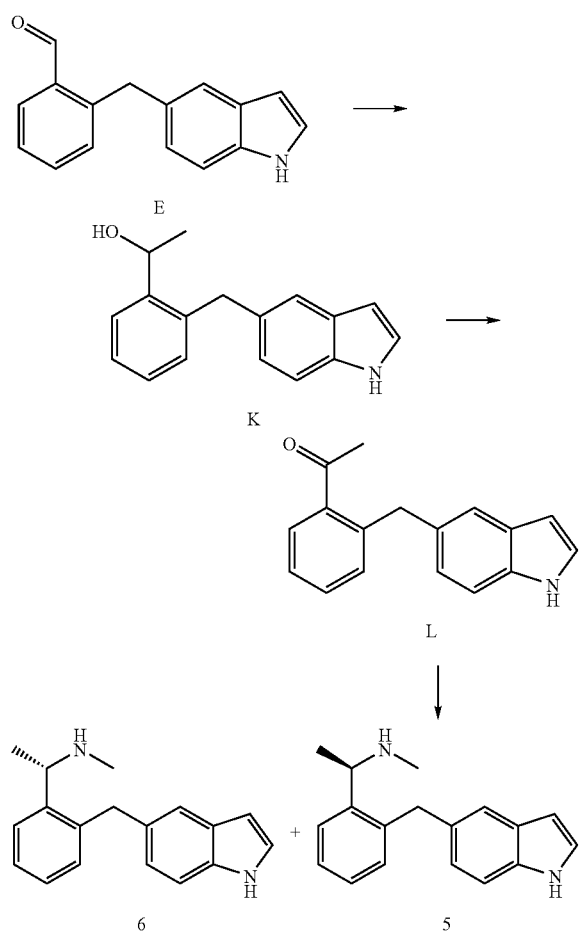

Preparation of intermediate E: See Example 2, above.
Preparation of intermediate K: To a stirred solution of E (0.68 g, 2.9 mmol) in THF at −78° C. was added dropwise a solution of methylmagnesium bromide (3.0 M in diethyl ether, 4.8 mL, 14 mmol). The reaction mixture was allowed to slowly warm to room temperature, and after stirring for 3 h, was quenched with saturated aqueous ammonium chloride. The resulting solution was partitioned between water and diethyl ether, and the ether layer was washed with brine, dried over sodium sulfate, filtered, and concentrated under reduced pressure. The crude residue so obtained was purified by flash chromatography (ethyl acetate/hexane) to afford K (0.62 g).

Preparation of intermediate L: To a solution of K (0.62 g, 2.5 mmol) in dichloromethane (20 mL) was added manganese(II) oxide (2.1 g, 25 mmol), and the resulting mixture was stirred at reflux for 16 h. The reaction mixture was filtered, concentrated under reduced pressure, and the crude residue so obtained was purified by flash chromatography (ethyl acetate/hexane) to afford L.

Preparation of 5 and 6: Intermediate L (0.10 g, 0.40 mmol) was mixed with titanium(IV) isopropoxide (0.2 g, 0.7 mmol), followed by addition of methanol (2 mL) and methylamine (33% solution in ethanol, 0.075 mL). The resulting mixture was stirred at room temperature for 4 h, at which time it was diluted with methanol (4 mL) and sodium borohydride (0.061 g, 1.6 mmol) was added. The resulting mixture was stirred at room temperature for 30 min, and was then treated with solid sodium bicarbonate. The mixture was filtered, and the filtrate concentrated under reduced pressure. The crude residue so obtained was purified via chiral HPLC by multiple injections onto 20×250 mm Chiralpak AD preparative column (ethanol/hexane) to afford the single enantiomers 5 and 6.

Similarly prepared compounds from Table I include compound 4.

Example 5

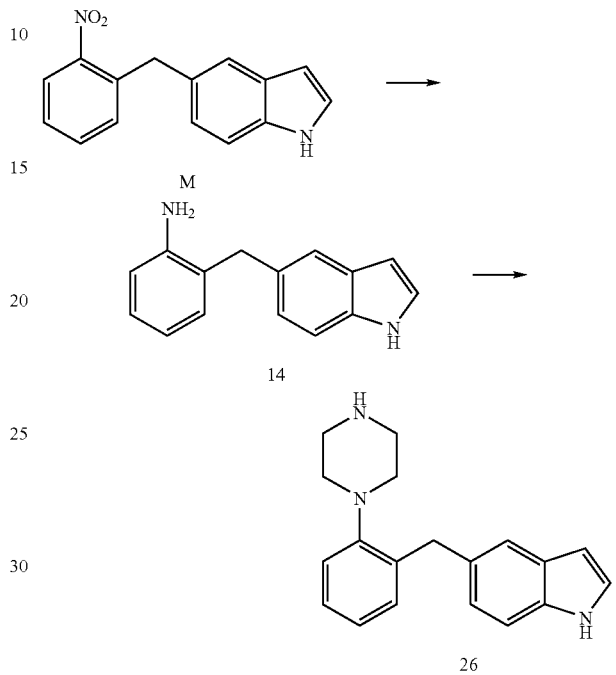

Preparation of intermediate M: A mixture of 2-nitrobenzylbromide (2.5 g, 12 mmol), indole-5-boronic acid (3.0 g, 19 mmol), tetrakis(triphenylphosphine)-palladium(0) (0.67 g, 0.58 mmol), and cesium fluoride (5.6 g, 37 mmol) in 1,2-dimethoxyethane (50 mL) was stirred at reflux for 3 h. The resulting dark brown suspension was filtered through diatomaceous earth, and the solids were washed with diethyl ether. The combined filtrates were concentrated under reduced pressure, and the crude product so obtained was purified by flash chromatography (ethyl acetate/hexane) to afford M as a pale yellow solid (1.3 g).

Preparation of 14: To a solution of M (1.1 g, 4.4 mmol) in ethanol (50 mL) was added 10% palladium on carbon (0.10 g, Degussa type), and the mixture was stirred under a balloon atmosphere of hydrogen for 16 h. The reaction mixture was filtered through diatomaceous earth and concentrated under reduced pressure to afford 14 as a light brown solid (0.92 g).

Preparation of 26: A mixture of 14 (0.82 g, 3.7 mmol), bis(chloroethylamine) hydrochloride (0.72 g, 4.1 mmol), and potassium carbonate (1.3 g, 9.2 mmol) in n-butanol (15 mL) were stirred and heated to reflux for 8 h. The reaction mixture was cooled to room temperature, concentrated under reduced pressure, and partitioned between water and dichloromethane. The dichloromethane extract was dried over sodium sulfate, filtered, and concentrated under reduced pressure. The crude residue so obtained was purified by flash chromatography (methanol/dichloromethane/aqueous ammonium hydroxide) to afford a white solid, which was dissolved in ethanol (5 mL), treated with hydrogen chloride (1.0 M in diethyl ether), and concentrated under reduced pressure to afford 26 as a light brown powder (0.17 g).

Similarly prepared compounds from Table I include compound 48.

Example 6

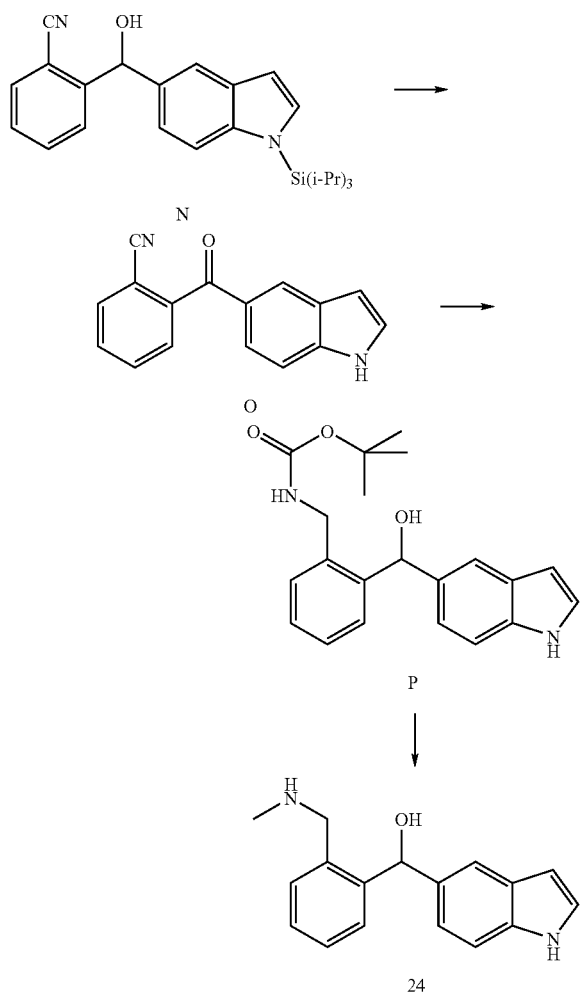

Preparation of intermediate N: To a mixture of 5-bromo-1-triisopropylsilylindole (12.9 g, 37 mmol) in THF (100 mL) at −78° C. was added dropwise a solution of tert-butyllithium (1.7M in pentane, 52 mL). The resulting mixture was stirred at −78° C. for 20 min, at which time a solution of 2-cyanobenzaldehyde (9.6 g, 73 mmol) in THF (75 mL) was added in one quick portion. The reaction mixture was stirred at −78° C. for 30 min, then allowed to warm to room temperature, at which time it was quenched with saturated aqueous ammonium chloride. The mixture was diluted with water and extracted with ethyl acetate, and the combined organic extracts were washed with brine, dried over sodium sulfate, filtered, and concentrated under reduced pressure. The crude residue so obtained was purified by flash chromatography (ethyl acetate/hexane) to afford N as a light yellow solid (6.1 g).

Preparation of intermediate O: To a slurry of N (3.2 g, 7.8 mmol) in DMSO (25 mL) was added triethylamine (9.8 g, 51 mmol), followed by a solution of sulfur trioxide-pyridine complex (3.7 g, 24 mmol) in DMSO (15 mL). The resulting mixture was stirred at room temperature for 16 h, then diluted with water and extracted with ethyl acetate. The combined organic extracts were washed with brine, dried over sodium sulfate, filtered, and concentrated under reduced pressure, and the crude residue so obtained was purified by flash chromatography (ethyl acetate/hexane) to afford O (1.6 g).

Preparation of intermediate P: To a solution of O (1.4 g, 5.9 mmol) in methanol was added di-tert-butyldicarbonate (2.6 g, 12 mmol) and nickel(II) chloride hexahydrate (0.14 g, 0.58 mmol), and the resulting mixture was cooled to 0° C., with stirring. Sodium borohydride (2.2 g, 59 mmol) was added portionwise, and resulting mixture was allowed to warm to room temperature and stirred for 16 h. Diethylenetriamine (0.67 g, 5.9 mmol) was added, and stirring was continued for 3 h. The methanol was removed by concentration under reduced pressure, and the residue so obtained was partitioned between ethyl acetate and saturated aqueous sodium bicarbonate. The ethyl acetate layer was dried over sodium sulfate, filtered, and concentrated under reduced pressure, and the crude residue so obtained was purified by flash chromatography (ethyl acetate/hexane) to afford P as a foam (1.0 g).

Preparation of 24: A solution of P (0.50 g, 1.4 mmol) in THF (5 mL) was treated with a solution of lithium aluminum hydride (1.0M in THF, 14 mL, 14 mmol), and the resulting mixture was stirred at reflux for 16 h. After cooling to room temperature, an aqueous solution of Rochelle's salt was added and stirred. The resulting mixture was extracted with ethyl acetate, and the combined organic extracts were washed with brine, dried over sodium sulfate, filtered, and concentrated under reduced pressure. The crude residue so obtained was purified by flash chromatography (methanol/dichloromethane/aqueous ammonium hydroxide) to afford 24 as a foam (0.28 g).

Example 7

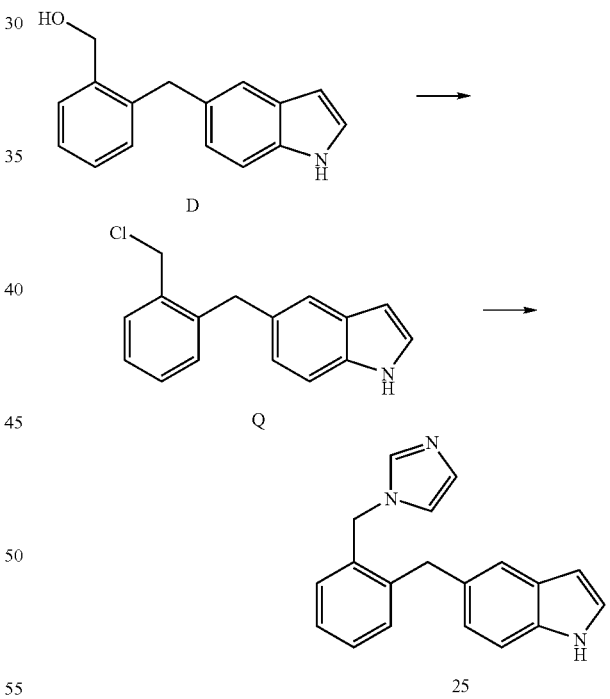

Preparation of intermediate D: See Example 2, above.
Preparation of intermediate Q: To a solution of D (0.99 g, 4.2 mmol) in carbon tetrachloride (20 mL) was added triphenylphosphine (2.2 g, 8.4 mmol), and the resulting mixture was stirred at reflux for 16 h. The crude product was adsorbed onto silica gel (5 g), and purified by flash chromatography (ethyl acetate/hexane) to afford Q as a yellow oil (0.26 g).

Preparation of 25: A solution containing Q (0.10 g, 0.39 mmol) and imidazole (0.13 g, 2.0 mmol) in DMSO (2.5 mL) was heated to 100° C., with stirring, for 4 h. The reaction mixture was cooled to room temperature and partitioned between water and ethyl acetate, and the organic layer was washed successively with water and brine, dried over sodium sulfate, filtered, and concentrated under reduced pressure. The crude residue so obtained was purified by flash chromatography (methanol/dichloromethane/aqueous ammonium hydroxide) to afford 25 as a grey foam (0.079 g).

Example 8

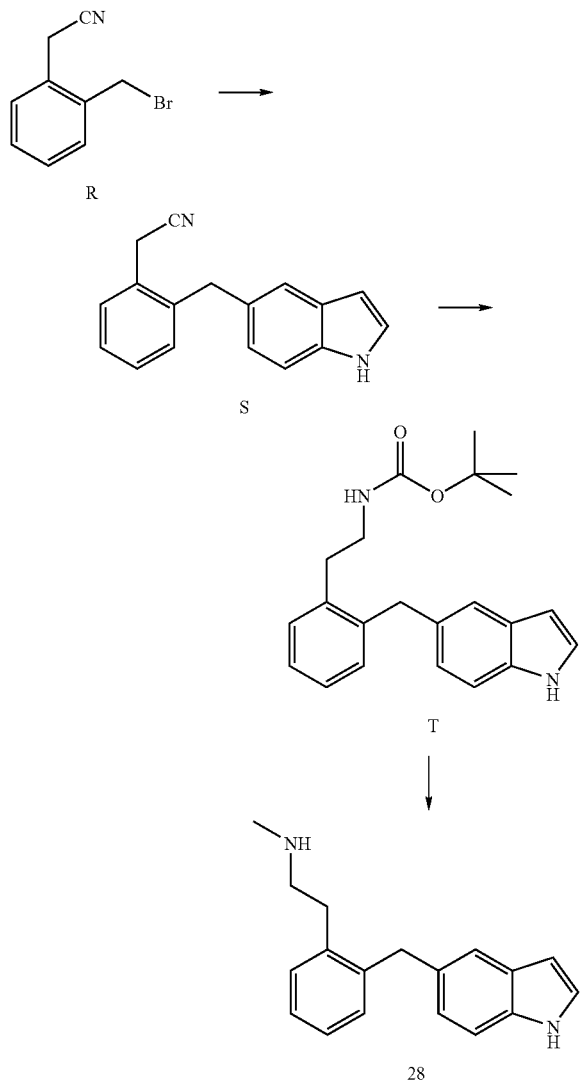

Preparation of intermediate R: A slurry of benzoyl peroxide (0.34 g, 0.98 mmol) and N-bromosuccinimide (6.8 g, 38 mmol) in carbon tetrachloride (40 mL) was heated to reflux, with stirring. To that slurry was added dropwise a solution of 2-methylphenylacetonitrile (5.0 g, 38 mmol) in carbon tetrachloride (30 mL). The resulting mixture was kept stirring at reflux for 4 h, and then cooled to room temperature, filtered, and concentrated under reduced pressure. The crude product so obtained was purified by flash chromatography (ethyl acetate/hexane) to afford R as a light yellow solid (3.2 g).

Preparation of intermediate S: A mixture of R (0.50 g, 2.4 mmol), indole-5-boronic acid (0.42 g, 2.6 mmol), tetrakis(triphenylphosphine)palladium(0) (0.14 g, 0.12 mmol), and cesium fluoride (1.1 g, 7.1 mmol) in 1,2-dimethoxyethane (11 mL) was stirred at 85° C. for 1 h. Upon cooling, the resulting dark brown suspension was filtered through diatomaceous earth, and the filtrate was partitioned between water and ethyl acetate. The organic layer was washed with brine, dried over sodium sulfate, filtered, and concentrated under reduced pressure, and the crude residue so obtained was purified by flash chromatography (ethyl acetate/hexane) to afford S as a yellow oil (0.20 g).

Preparation of intermediate T: To a solution of S (0.20 g, 0.81 mmol) in methanol (8 mL) at 0° C. was added di-tert-butyldicarbonate (0.35 g, 1.6 mmol) and nickel(II) chloride hexahydrate (0.02 g, 0.08 mmol), followed by portionwise addition of sodium borohydride (0.30 g, 8.1 mmol). The reaction mixture was stirred at room temperature and stirred for 16 h and diethylenetriamine (0.67 g, 5.9 mmol) was added, and stirring was continued for 3 h. The methanol was removed by concentration under reduced pressure, and the residue so obtained was partitioned between ethyl acetate and saturated aqueous sodium bicarbonate. The ethyl acetate layer was dried over sodium sulfate, filtered, and concentrated under reduced pressure to afford T (0.10 g).

Preparation of 28: A solution of T (0.66 g, 1.9 mmol) in THF (18 mL) was treated with a solution of lithium aluminum hydride (1.0M in THF, 12 mL, 12 mmol), and the resulting mixture was stirred at reflux for 16 h. After cooling to room temperature, aqueous sodium hydroxide (2.5 N) was added dropwise and the resulting precipitate was removed by filtration through diatomaceous earth. The filtrate was concentrated under reduced pressure, and the crude residue so obtained was purified by flash chromatography (methanol/dichloromethane/aqueous ammonium hydroxide) to afford 28 as a white solid (0.41 g).

Example 9

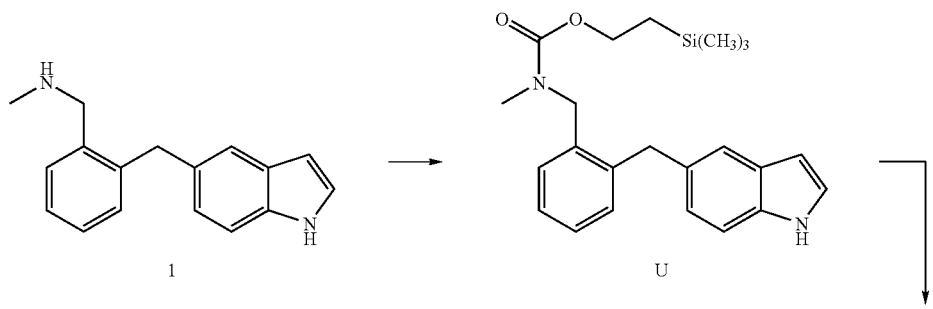

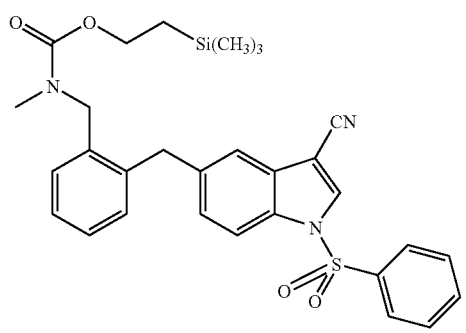

W

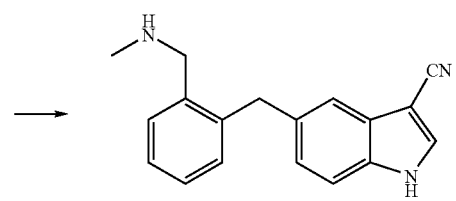

V

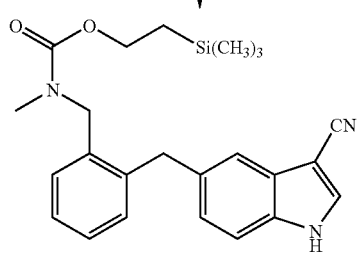

X

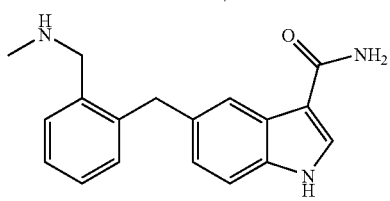

29

30

Preparation of 1 (free base): see Example 1, above. Preparation of intermediate U: To a slurry of 1 (0.10 g, 0.42 mmol) in water (2 mL) was added triethylamine (0.12 g, 0.63 mmol) and dioxane (2 mL). Solid 2-(trimethylsilyl)ethylcarbonate-O-succinimide (0.12 g, 0.46 mmol) was added and the resulting mixture was stirred at room temperature for 16 h. Ether was added, and the mixture was washed successively with saturated aqueous ammonium chloride and brine, dried over sodium sulfate, filtered, and concentrated under reduced pressure, and the crude residue so obtained was purified by flash chromatography (ethyl acetate/hexane) to afford U as a colorless oil (0.15 g).

Preparation of intermediate V: To a solution of U (0.60 g, 1.5 mmol) in DMF (8 mL) was added crushed potassium hydroxide (0.21 g, 3.8 mmol), followed by dropwise addition of a solution of iodine (0.38 g, 1.5 mmol) in DMF (2 mL). After stirring at room temperature for 45 min, 10% aqueous sodium sulfite was added and the mixture was extracted with ether and ethyl acetate. The organic layer was washed successively with water and brine, dried over magnesium sulfate, filtered, and concentrated under reduced pressure. The residue so obtained was dissolved in DMF (8 mL), and sodium hydride (0.12 g, 3.0 mmol) was added. After stirring the resulting mixture at room temperature for 30 min, benzenesulfonyl chloride (0.32 g, 1.8 mmol) was added, and stirring continued for 16 h. Water was added, and the mixture was extracted with diethyl ether. The organic layer was washed successively with water and brine, dried over sodium sulfate, filtered, and concentrated under reduced pressure. The crude residue so obtained was purified by flash chromatography (ethyl acetate/hexane) to afford V (0.16 g).

Preparation of intermediate W: A mixture of V (0.16 g, 0.24 mmol), cuprous cyanide (0.087 g, 0.97 mmol), tris(dibenzylideneacetone)dipalladium (0.011 g, 0.012 mmol) and diphenylphosphinoferrocene (0.027 g, 0.048 mmol) in dioxane (3 mL) was heated reflux, with stirring, for 1 h. Upon cooling to room temperature, the mixture was filtered and the solids washed with ethyl acetate. The combined filtrates were concentrated under reduced pressure and the crude residue so obtained was purified by flash chromatography (ethyl acetate/hexane) to afford W as a white foam (0.12 g).

Preparation of intermediate X: A solution of W (0.69 g, 1.2 mmol) and potassium carbonate (0.51 g, 3.7 mmol) in methanol (10 mL) and water (2 mL) was stirred at room temperature for 1 h. The mixture was diluted with water and extracted with dichloromethane. The organic layer was washed with brine, dried over sodium sulfate, filtered, and concentrated under reduced pressure, and the crude residue so obtained was purified by flash chromatography (ethyl acetate/hexane) to afford X.

Preparation of 29: To a solution of X (0.64 g, 1.5 mmol) in THF was added a solution of tetrabutylammonium fluoride (1.0 M in THF, 6 mL, 6 mmol), and the resulting mixture was heated at 60° C. for 2 h. Upon cooling to room temperature, the mixture was diluted with water and extracted with ethyl acetate, and the organic layer was washed successively with water and brine, dried over sodium sulfate, filtered, and concentrated under reduced pressure. The crude residue so obtained was purified by flash chromatography (methanol/dichloromethane/aqueous ammonium hydroxide) to afford 30 (0.20 g).

Preparation of 30: A mixture of 29 (0.13 g, 0.47 mmol) and potassium hydroxide (0.40 g, 7.1 mmol) in ethanol (2 mL) and water (2 mL) was subjected to heating under microwave irradiation at 150° C. for 1 h. Concentration under reduced pressure followed by flash chromatography (methanol/dichloromethane/aqueous ammonium hydroxide) afforded 30 (0.050 g).

Example 10

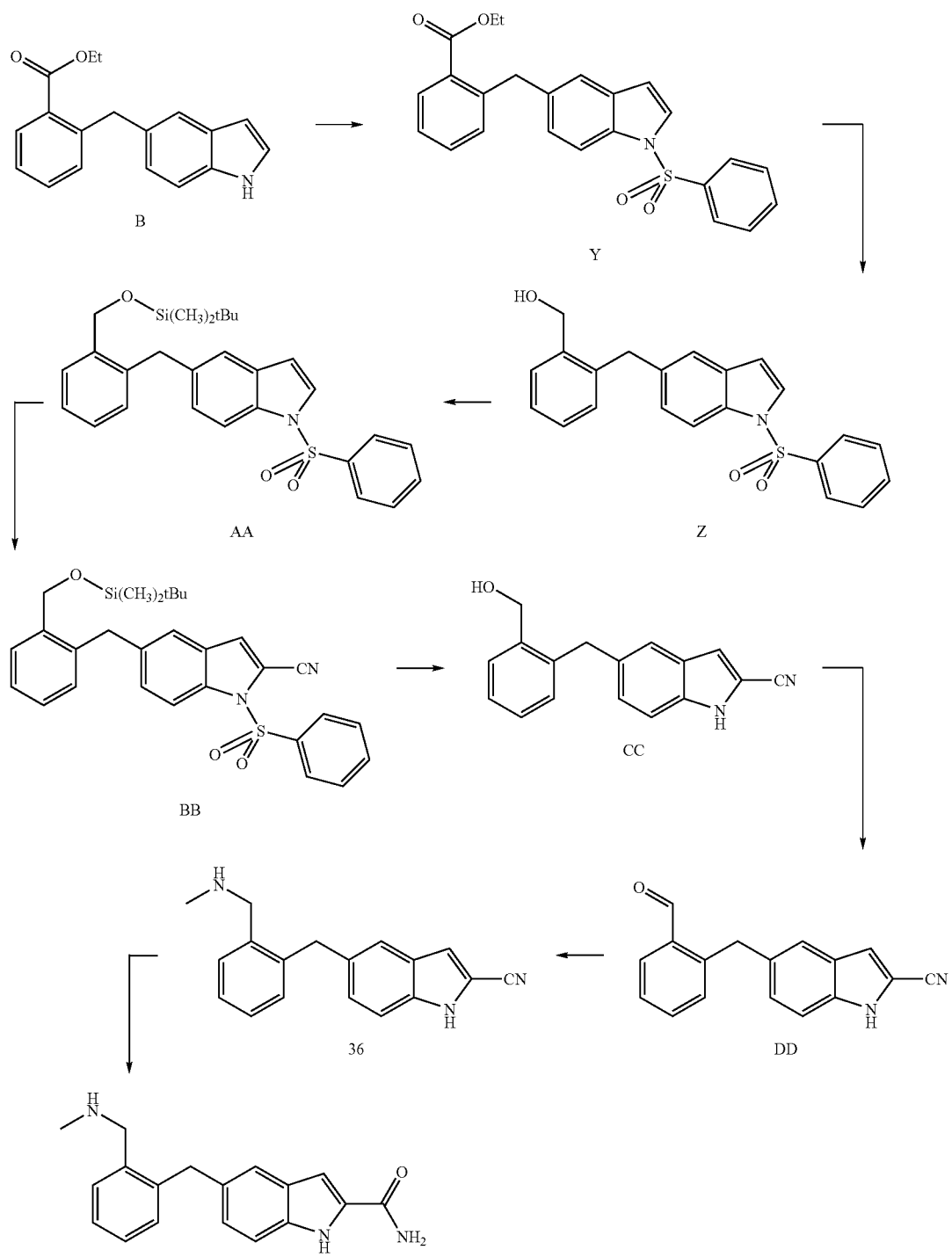

Preparation of B: see Example 1, above. Preparation of intermediate Y: To a solution of B (0.85 g, 3.1 mmol) in DMF (15 mL) was added sodium hydride (0.18 g, 4.6 mmol), followed by benzenesulfonyl chloride (0.65 g, 3.7 mmol). The resulting mixture was stirred at room temperature for 16 h, diluted with water, and extracted with diethyl ether. The organic layer was washed with brine, dried over sodium sulfate, filtered, and concentrated under reduced pressure, and the crude residue so obtained was purified by flash chromatography (ethyl acetate/hexane) to afford Y (0.64 g).

Preparation of intermediate Z: A stirred solution of Y (0.64 g, 1.5 mmol) in THF (15 mL) was treated with a solution of lithium aluminum hydride (1.0M in THF, 1.6 mL, 1.6 mmol) at 0° C., and the resulting mixture was stirred at 0° C. for 1.5 h. A few drops of water, followed by an aqueous solution of Rochelle's salt and then ethyl acetate was added and stirred at room temperature. The resulting mixture was extracted with ethyl acetate, and the combined organic extracts were washed with brine, dried over sodium sulfate, filtered, and concentrated under reduced pressure. The crude residue so obtained was purified by flash chromatography (ethyl acetate/hexane) to afford Z as an oil (0.49 g).

Preparation of intermediate AA: A mixture of Z (0.49 g, 1.3 mmol), tert-butyldimethylsilyl chloride (0.21 g, 1.4 mmol) and imidazole (0.10 g, 1.5 mmol) in DMF (10 mL) was stirred at room temperature for 16 h. The reaction mixture was then diluted with water, and extracted with diethyl ether. The organic layer was washed with brine, dried over sodium sulfate, filtered, and concentrated under reduced pressure, and the crude residue so obtained was purified by flash chromatography (ethyl acetate/hexane) to afford AA as a colorless oil (0.52 g).

Preparation of intermediate BB: To a stirred solution of AA (0.095 g, 0.19 mmol) and N,N,N',N'-tetramethylethylenediamine (0.045 g, 0.39 mmol) in THF at −78° C. was added dropwise a solution of tert-butyllithium (1.7 M in pentane, 0.25 mL, 0.42 mmol). After stirring at −78° C. for 1 h, a solution of phenyl cyanate (0.035 g, 0.29 mmol) in THF was added, and stirring at −78° C. was then continued for 1.5 h, followed by stirring at 0° C. for 1 h. Saturated aqueous ammonium chloride solution was added, and the reaction mixture was then diluted with water, and extracted with diethyl ether. The organic layer was washed with brine, dried over sodium sulfate, filtered, and concentrated under reduced pressure, and the crude residue so obtained was purified by flash chromatography (ethyl acetate/hexane) to afford BB (0.058 g).

Preparation of intermediate CC: To a solution of BB (0.058 g, 0.11 mmol) in THF (3 mL) was added a solution of tetrabutylammonium fluoride (1.0 M in THF, 0.16 mL, 0.16 mmol), and the resulting mixture was heated at reflux for 2 h. Upon cooling to room temperature, the mixture was diluted with water and extracted with ethyl acetate, and the organic layer was washed with brine, dried over sodium sulfate, filtered, and concentrated under reduced pressure. The crude residue so obtained was purified by flash chromatography (ethyl acetate/hexane) to afford CC (0.021 g).

Preparation of intermediate DD: To a solution of CC (0.15 g, 0.57 mmol) in dichloromethane (5 mL) was added activated manganese (IV) oxide (0.50 g, 5.7 mmol). The resulting black suspension was stirred at reflux for 16 h, and was filtered while still hot through a glass microfiber filter. The filtrate was concentrated under reduced pressure, and the crude residue so obtained purified by flash chromatography (ethyl acetate/hexane) to afford E as a light brown solid (0.080 g).

Preparation of 36: To a solution of DD (0.08 g, 0.3 mmol) in ethanol was added methylamine (33% solution in ethanol, 0.7 mL), and the resulting mixture was stirred for 4 h at room temperature. Sodium borohydride (0.023 g, 0.6 mmol) was added, and stirring continued for 10 min. Saturated aqueous sodium bicarbonate was added, and the crude residue was adsorbed onto silica gel and purified by flash chromatography (methanol/dichloromethane/aqueous ammonium hydroxide) to afford 36 as a white foam (0.097 g).

Preparation of 40: A solution of 36 (0.050 g, 0.18 mmol) in ethanol (2 mL) was treated with an aqueous sodium hydroxide solution (2.5 N, 0.72 mL, 1.8 mmol) and the resulting mixture was heated to 60° C. for 2 h followed by 80° C. for 30 min. The mixture was filtered through diatomaceous earth, solids washed with dichloromethane, and the filtrate concentrated under reduced pressure followed by flash chromatography (methanol/dichloromethane/aqueous ammonium hydroxide) to afford 40 (0.010 g).

Example 11

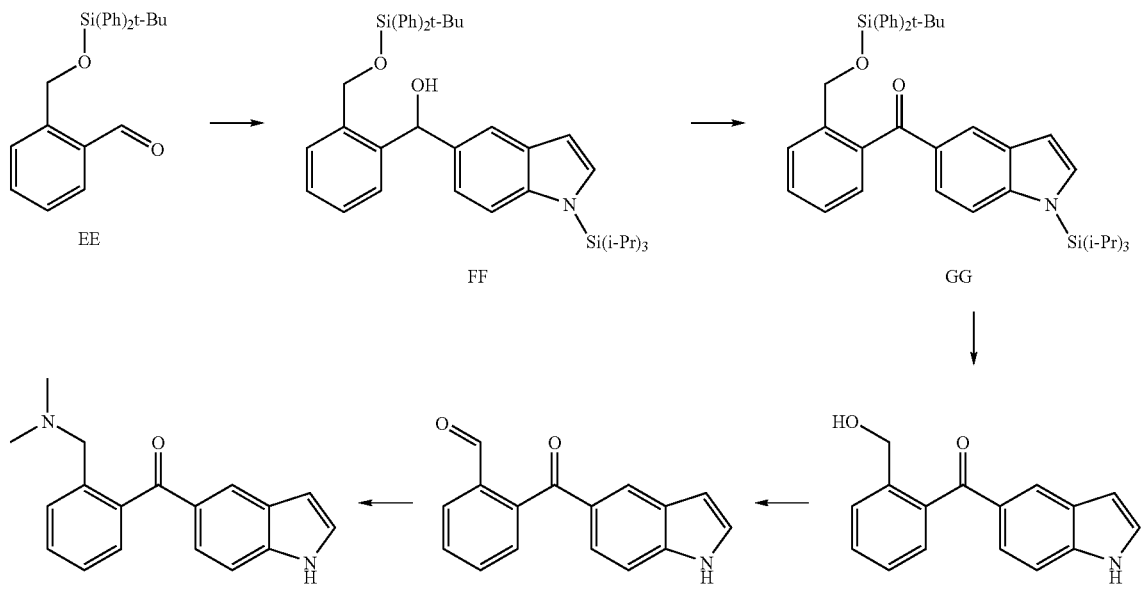

For preparation of intermediate EE: see *Chem. Eur. J.* 1997, 3, 399. Preparation of intermediate FF: To a mixture of 5-bromo-1-triisopropylsilylindole (1.8 g, 5.0 mmol) in diethyl ether (40 mL) at −78° C. was added dropwise a solution of tert-butyllithium (1.7M in pentane, 6.5 mL, 11 mmol). The resulting mixture was stirred at −78° C. for 15 min, at which time a solution of EE (1.9 g, 5.1 mmol) in diethyl ether (20 mL) was added in one quick portion. The reaction mixture was stirred at −78° C. for 1 h, at which time it was quenched with saturated aqueous ammonium chloride. The mixture was diluted with water and extracted with diethyl ether, and the combined organic extracts were washed with brine, dried over sodium sulfate, filtered, and concentrated under reduced pressure. The crude residue so obtained was purified by flash chromatography (ethyl acetate/hexane) to afford FF as a white foam (2.4 g).

Preparation of intermediate GG: To a solution of FF (0.60 g, 0.92 mmol) in dichloroethane (10 mL) was added activated manganese (IV) oxide (0.80 g, 9.2 mmol). The resulting black suspension was stirred at reflux for 3 h, and was cooled to room temperature and then filtered. The filtrate was concentrated under reduced pressure, and the crude residue so obtained purified by flash chromatography (ethyl acetate/hexane) to afford GG (0.59 g).

Preparation of intermediate HH: To a solution of GG (0.59 g, 0.92 mmol) in THF (10 mL) was added tetramethylammonium fluoride tetrahydrate (0.3 g, 1.8 mmol), and the resulting mixture was stirred at room temperature for 3 h. A solution of tetrabutylammonium fluoride (1.0 M in THF, 0.92 mL, 0.92 mmol) was added, and stirring continued for 1 h. The mixture was diluted with water and extracted with ethyl acetate, and the combined organic extracts were washed with brine, dried over sodium sulfate, filtered, and concentrated under reduced pressure. The crude residue so obtained was purified by flash chromatography (ethyl acetate/hexane) to afford HH (0.23 g).

Preparation of intermediate II: To a solution of HH (0.23 g, 0.91 mmol) in dichloromethane (9 mL) was added activated manganese (IV) oxide (0.80 g, 9.2 mmol). The resulting black suspension was stirred at reflux for 3 h, and was cooled to room temperature and then filtered. The filtrate was concentrated under reduced pressure, and the crude residue so obtained purified by flash chromatography (ethyl acetate/hexane) to afford II as a white foam (0.16 g).

Preparation of 37: To a solution of II (0.16 g, 0.66 mmol) and dimethylamine (1.3 mmol; from 0.65 mL of a 2.0 M solution in THF) in dichloromethane (6 mL) was added sodium triacetoxyborohydride (0.21 g, 0.97 mmol). The mixture was stirred at room temperature for 16 h. A solution of saturated aqueous sodium bicarbonate was added, and the mixture was diluted with water and extracted with dichloromethane. The organic layer was dried over sodium sulfate, filtered and concentrated under reduced pressure, and the crude residue so obtained was purified by flash chromatography (methanol/dichloromethane/aqueous ammonium hydroxide) to afford 37 as a light pink foam (0.13 g).

Example 12

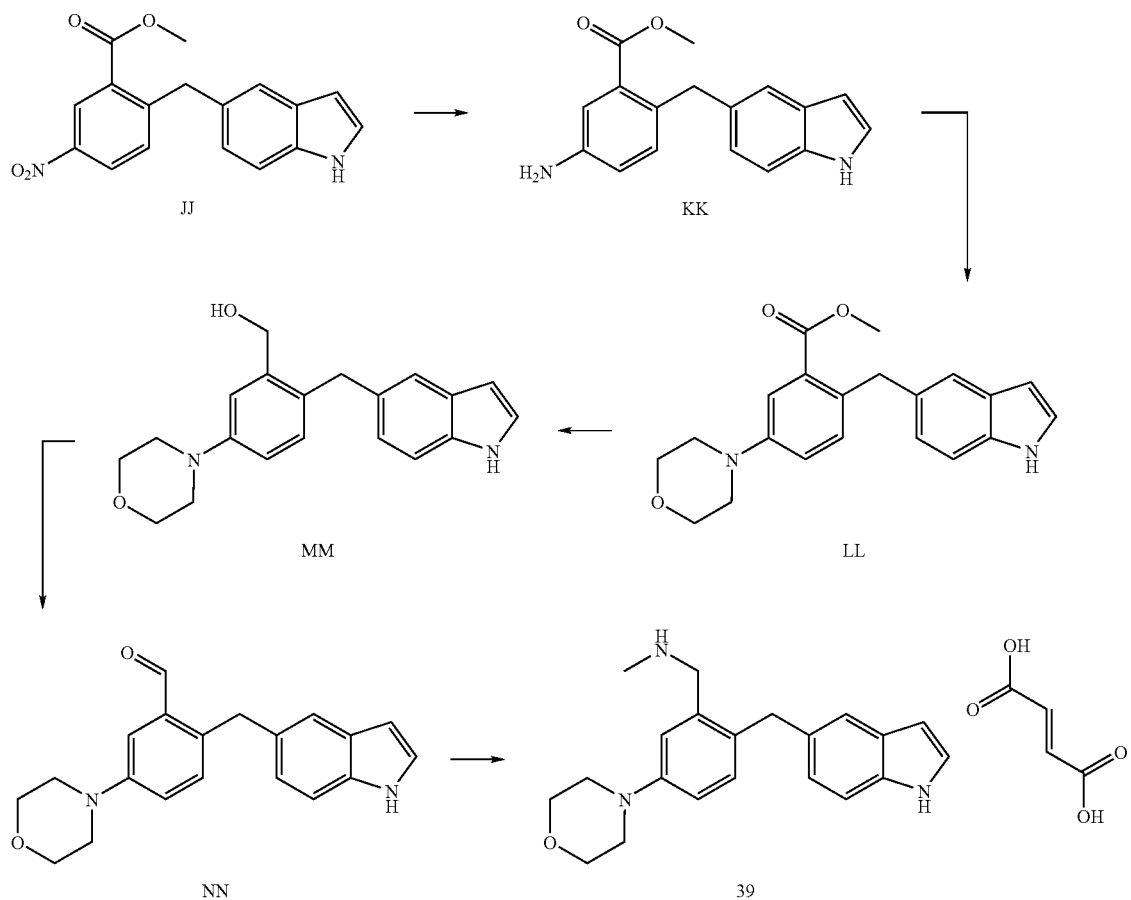

Preparation of intermediate JJ: A mixture of methyl 2-bromomethyl-5-nitrobenzoate (0.45 g, 1.6 mmol), indole-5-boronic acid (0.42 g, 2.6 mmol), tetrakis(triphenylphosphine)palladium(0) (0.095 g, 0.082 mmol), and cesium fluoride (0.80 g, 5.3 mmol) in 1,2-dimethoxyethane (10 mL) was stirred at reflux for 4 h. Upon cooling to room temperature, the reaction mixture was diluted with water and extracted with ethyl acetate. The combined organic extracts were washed successively with water and brine, dried over sodium sulfate, filtered, and concentrated under reduced pressure. The residue so obtained was purified by flash chromatography (ethyl acetate/hexane) to afford JJ as a yellow oil (0.18 g).

Preparation of intermediate KK: To a solution of JJ (0.17 g, 0.55 mmol) in methanol (2 mL) and ethyl acetate (0.5 mL) was added 10% palladium on carbon (0.011 g). The reaction mixture was stirred under a hydrogen balloon atmosphere for 2.5 h, then filtered through diatomaceous earth, which was rinsed with methanol. The combined filtrate was concentrated under reduced pressure to afford KK as a yellow solid (0.16 g).

Preparation of intermediate LL: A mixture of KK (0.15 g, 0.54 mmol), bis(2-bromoethyl)ether (0.12 g, 0.54 mmol), and ethyldiisopropylamine (0.16 g, 1.3 mmol) in toluene (0.7 mL) was stirred at 110° C. for 16 h. Upon cooling to room temperature, the reaction mixture was diluted with water and extracted with ethyl acetate. The combined organic extracts were washed successively with water and brine, dried over sodium sulfate, filtered, and concentrated under reduced pressure. The residue so obtained was purified by flash chromatography (ethyl acetate/hexane) to afford LL as a yellow solid (0.12 g).

Preparation of intermediate MM: A stirred suspension of LL (0.12 g, 0.34 mmol) in THF (3 mL) was treated with a solution of lithium aluminum hydride (1.0M in THF, 0.38 mL, 3.8 mmol) at 0° C., and the resulting mixture was stirred at 0° C. for 2 h. Crushed sodium sulfate decahydrate was added, and the mixture was allowed to warm to room temperature and stirred for 2 h. The solids were removed by filtration, washed with dichloromethane and methanol, and the combined filtrates were concentrated under reduced pressure. The crude residue so obtained was partitioned between dichloromethane and water, and the combined organic extracts were washed with brine, dried over sodium sulfate, filtered, and concentrated under reduced pressure to afford MM as a yellow solid (0.11 g).

Preparation of intermediate NN: To a solution of MM (0.10 g, 0.31 mmol) in dichloromethane (4 mL) was added activated manganese (IV) oxide (0.39 g, 4.5 mmol). The resulting black suspension was stirred at reflux for 3 h, at which time an additional portion of activated manganese (IV) oxide (0.39 g, 4.5 mmol) was added, and stirring at reflux was continued for 16 h. The warm mixture was filtered, and the filtrate was concentrated under reduced pressure, and the crude residue so obtained purified by flash chromatography (ethyl acetate/hexane) to afford II as a yellow solid (0.042 g).

Preparation of 39: To a solution of NN (0.040 g, 0.12 mmol) in methanol (0.3 mL) was added methylamine (33% solution in ethanol, 0.23 mL), and the resulting mixture was stirred for 16 h at room temperature. Dichloromethane (0.3 mL) was added, and stirring continued for 3 h. Sodium borohydride (0.009 g, 0.2 mmol) was added, and stirring continued for 1.5 h. Saturated aqueous sodium bicarbonate was added, and the mixture was extracted with ethyl acetate. The organic layer was washed successively with water and brine, dried over sodium sulfate, filtered, and concentrated under reduced pressure. The residue so obtained was purified by flash chromatography (methanol/dichloromethane/aqueous ammonium hydroxide) to afford the free base of 39 as a light yellow solid (0.043 g, 0.13 mmol), which was dissolved in methanol (0.15 mL) and treated with fumaric acid (0.015 g, 0.13 mmol). The mixture was diluted with diisopropyl ether (1 mL), filtered, and dried under vacuum to afford 39 as a fumarate salt, a light pink powder (0.041 g).

Example 13

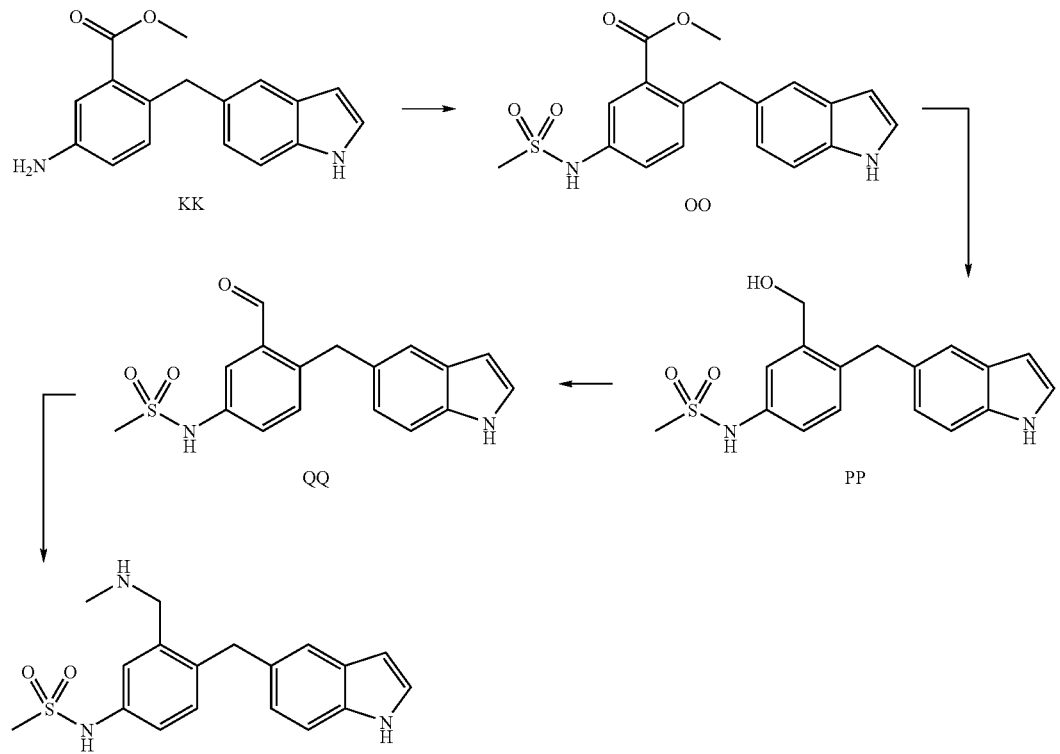

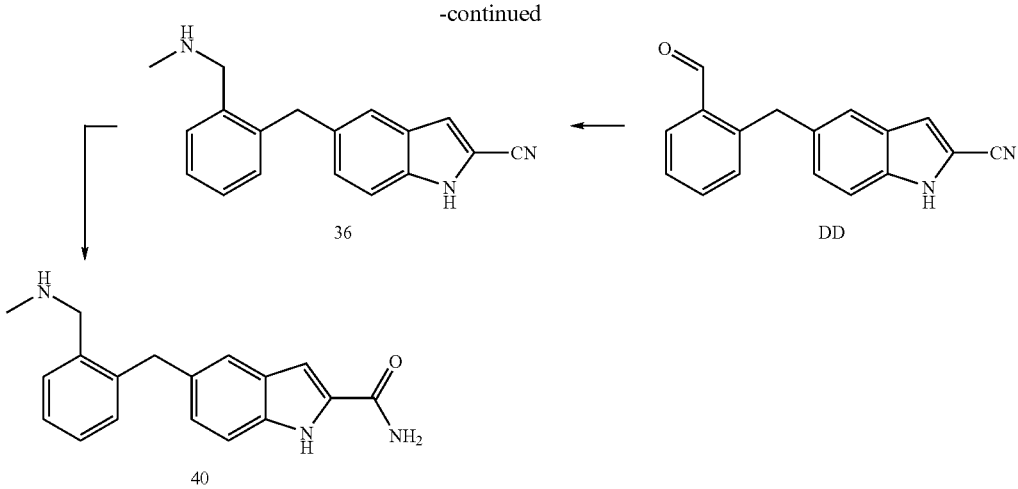

For preparation of intermediate KK: see Example 12, above. Preparation of intermediate OO: A solution of KK (0.17 g, 0.61 mmol) in dichloromethane (10 mL) was cooled to 0° C., and then triethylamine (0.081 g, 0.79 mmol) was added, followed by methanesulfonyl chloride (0.078 g, 0.67 mmol). Stirring was continued at 0° C. for 2 h, followed by stirring at room temperature for 20 h. The reaction mixture was cooled to 0° C., and additional triethylamine (0.02 mL) and methanesulfonyl chloride (0.01 mL) were added, followed by stirring at room temperature for 3 h. The reaction mixture was diluted with water and extracted with dichloromethane, and the organic layer was dried over sodium sulfate, filtered, and concentrated under reduced pressure. The residue so obtained was purified by flash chromatography (ethyl acetate/hexane) to afford OO as a light yellow oil (0.14 g).

Preparation of intermediate PP: A stirred suspension of MM (0.12 g, 0.33 mmol) in THF (3 mL) was treated with a solution of lithium aluminum hydride (1.0M in THF, 0.38 mL, 3.8 mmol) at 0° C., and the resulting mixture was stirred at 0° C. for 2 h. Crushed sodium sulfate decahydrate was added, and the mixture was allowed to warm to room temperature and stirred for 2 h. The solids were removed by filtration, washed with dichloromethane and methanol, and the combined filtrates were concentrated under reduced pressure. The crude residue so obtained was partitioned between dichloromethane and water, and the combined organic extracts were washed with brine, dried over sodium sulfate, filtered, and concentrated under reduced pressure. The crude residue so obtained was purified by flash chromatography (ethyl acetate/hexane) to afford PP as a light yellow solid (0.069 g).

Preparation of intermediate QQ: To a solution of PP (0.066 g, 0.20 mmol) in dichloroethane (2.5 mL) was added activated manganese (IV) oxide (0.24 g, 2.4 mmol). The resulting black suspension was stirred at reflux for 2.5 h. The warm mixture was filtered, and the filtrate was concentrated under reduced pressure to afford QQ as a brown solid (0.079 g, 80% purity).

Preparation of 41: To QQ (0.076 g, 80% purity, 0.19 mmol) in was added a solution of methylamine (33% in ethanol, 0.35 mL), and the resulting mixture was stirred for 16 h at room temperature. Sodium borohydride (0.014 g, 0.37 mmol) was added, and stirring continued for 1.5 h. Saturated aqueous sodium bicarbonate was added, and the mixture was extracted with dichloromethane. The organic layer was dried over sodium sulfate, filtered, and concentrated under reduced pressure. The residue so obtained was purified by flash chromatography (methanol/dichloromethane/aqueous ammonium hydroxide) to afford 41 as an off-white foam (0.037 g).

Example 14

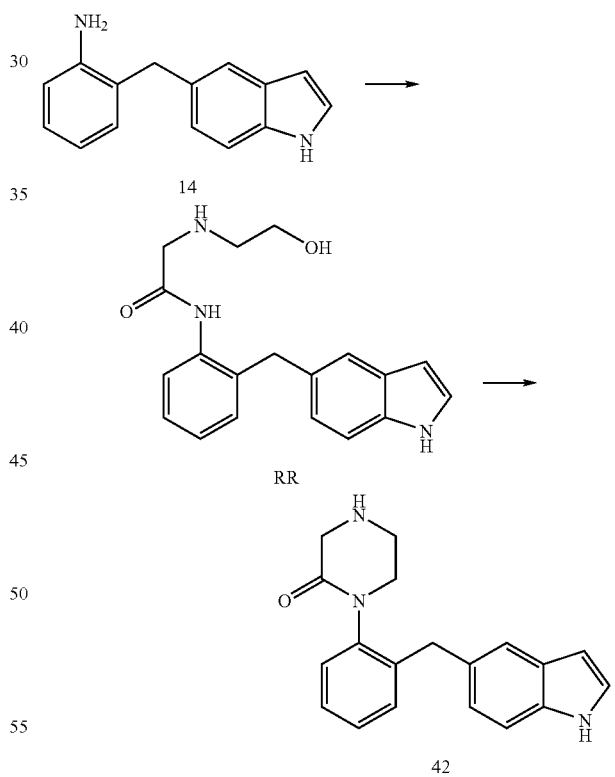

For preparation of 14: see Example 5, above. Preparation of intermediate RR: To a solution of potassium bicarbonate (0.17 g, 1.7 mmol) in water (1 mL) was added a solution of 14 (0.20 g, 0.90 mmol) in isopropyl acetate (1.5 mL). The resulting mixture was cooled, with stirring, to 0° C., and chloroacetyl chloride (0.14 g, 1.2 mmol) was added dropwise over 10 min. The mixture was then stirred at room temperature for 1 h, and the aqueous layer was removed and to the organic layer was added ethanolamine (0.21 g, 3.4 mmol) and the resulting mixture was stirred at 70° C. for 16 h. Additional ethanolamine (0.55 g, 9.0 mmol) was added, and stirring continued at 55° C. for 3 h. The reaction mixture was cooled to room temperature, partitioned between water and isopropyl acetate, and the organic layer was washed successively with water and brine, dried over sodium sulfate, filtered, and concentrated under reduced pressure. The residue so obtained was purified by flash chromatography (methanol/dichloromethane/aqueous ammonium hydroxide) to afford RR as a light brown oil (0.15 g).

Preparation of 42: To a solution of tri-n-butylphosphine (0.12 g, 0.59 mmol) in ethyl acetate (0.5 mL) at −10° C. was added diisopropylazodicarboxylate (0.13 g, 0.59 mmol), and the resulting solution was added dropwise to a solution of RR (0.15 g, 0.46 mmol) in ethyl acetate (1 mL) at −10° C. The resulting mixture was stirred at room temperature for 1.5 h, then diluted with water and extracted with ethyl acetate. The combined extracts were washed successively with water and brine, dried over sodium sulfate, filtered, and concentrated under reduced pressure. The residue so obtained was purified by flash chromatography (methanol/dichloromethane/aqueous ammonium hydroxide) to afford 42 as an off-white foam (0.069 g).

Example 15

Preparation of intermediate SS: A mixture of 1-benzyloxy-2-bromomethyl-benzene (1.6 g, 5.8 mmol), indole-5-boronic acid (1.5 g, 10 mmol), tetrakis-(triphenylphosphine)palladium(0) (0.34 g, 0.29 mmol), and cesium fluoride (2.9 g, 19 mmol) in 1,2-dimethoxyethane (30 mL) was stirred at 85° C. for 16 h. The reaction mixture was cooled to room temperature, partitioned between water and ethyl acetate, and the organic layer was washed successively with water and brine, dried over sodium sulfate, filtered, and concentrated under reduced pressure. The residue so obtained was purified by flash chromatography (ethyl acetate/hexane) to afford SS as a yellow oil (1.1 g).

Preparation of intermediate TT: To a stirred solution of SS (1.2 g, 3.8 mmol) in DMF (14 mL) at 0° C. was added sodium hydride (60 % dispersion, 0.45 g, 11 mmol), and the mixture was stirred 30 min, followed by dropwise addition of benzenesulfonyl chloride (0.79 g, 4.5 mmol). The resulting mixture was stirred at 0° C. for 1 h and at room temperature for 48 h, diluted with water, and extracted with ethyl acetate. The organic layer was washed sequentially with water and brine, dried over sodium sulfate, filtered, and concentrated under reduced pressure, and the crude residue so obtained was purified by flash chromatography (ethyl acetate/hexane) to afford TT as a yellow oil (0.83 g).

Preparation of intermediate UU: To a solution of TT (0.79 g, 2.0 mmol) in methanol (4 mL) and ethyl acetate (1 mL) was

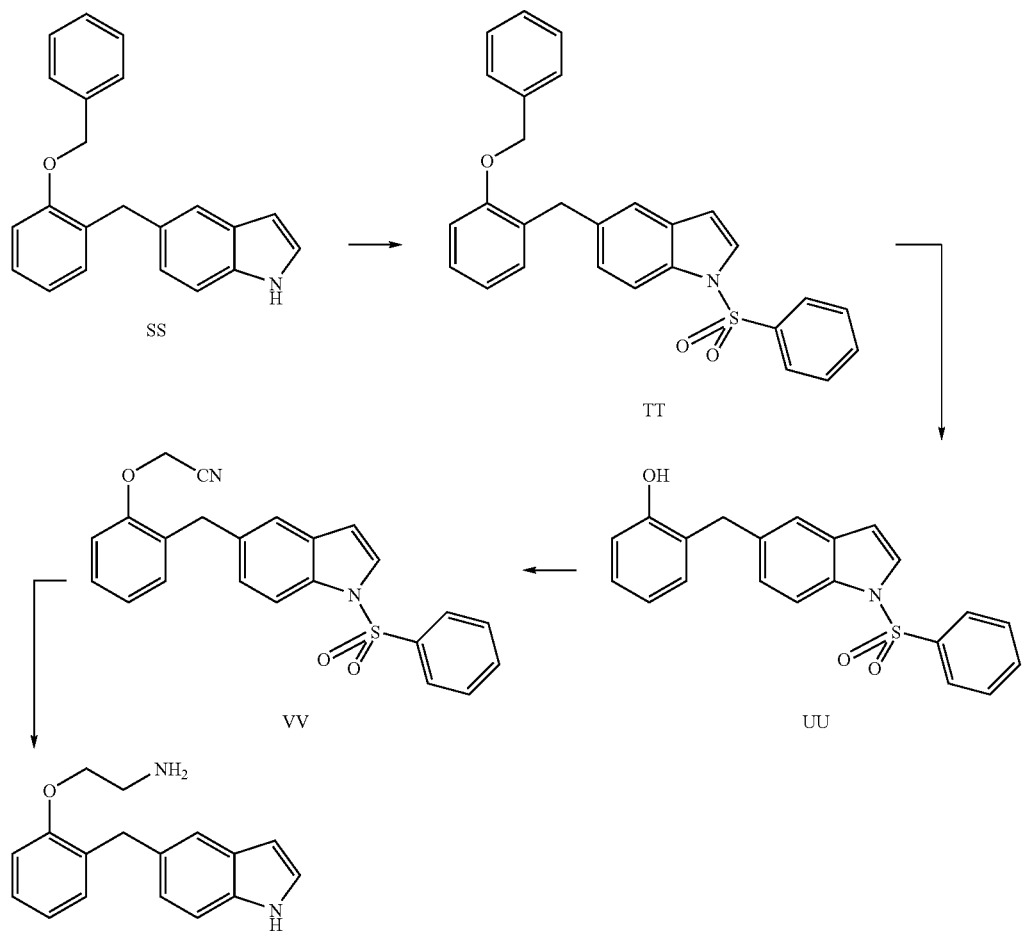

added 20% Pd(OH)$_2$ on carbon (0.082 g), and the mixture was shaken under hydrogen (50 psi) for 16 h. The reaction mixture was filtered through diatomaceous earth, which was rinsed with methanol, and the filtrate was concentrated under reduced pressure. The crude residue so obtained was purified by flash chromatography (ethyl acetate/hexane) to afford UU as a yellow oil (0.19 g).

Preparation of intermediate W: A mixture of UU (0.17 g, 0.47 mmol) and potassium carbonate (0.26 g, 1.9 mmol) in acetone (5 mL) was treated dropwise with a solution of bromoacetonitrile (0.069 g, 0.58 mmol) in acetone (2.5 mL). The reaction mixture was stirred and heated to 40° C. for 2 h. Upon cooling to room temperature, the mixture was filtered, and the filtrate was diluted with water and extracted with dichloromethane. The combined extracts were dried over sodium sulfate, filtered and concentrated under reduced pressure to afford W as a brown oil (0.20 g).

Preparation of 46: To a solution of W (0.2 g, 0.5 mmol) in THF (4.5 mL) was added a solution of lithium aluminum hydride in THF (1 M, 1.8 mL, 1.8 mmol) dropwise over 10 min. The mixture was stirred and heated to reflux for 2.5 h, then cooled to 0° C. and treated with pulverized sodium sulfate decahydrate until no bubbling was noted. An aqueous solution of Rochelle's salt (1 M, 10 mL) was added, and the resulting mixture was stirred at room temperature for 16 h. Added water and extracted with dichloromethane, and the combined organic extracts were dried over sodium sulfate, filtered, and concentrated under reduced pressure. The brown oily residue so obtained was purified by flash chromatography (methanol/dichloromethane/aqueous ammonium hydroxide) to afford 46 as a light brown solid (0.013 g).

Example 16 nesulfonyl chloride (0.25 g, 1.4 mmol). The resulting mixture was stirred at 0° C. for 1 h and at room temperature for 6 days, diluted with water, and extracted with ethyl acetate. The organic layer was washed sequentially with water and brine, dried over sodium sulfate, filtered, and concentrated under reduced pressure, and the crude residue so obtained was purified by flash chromatography (ethyl acetate/hexane) to afford WW as a yellow oil (0.14 g).

Preparation of intermediate XX: To a solution of nitromethane (0.044 g, 0.72 mmol) in THF (1 mL) at −76° C. was added dropwise a solution of n-butyllithium (1.6 M in hexane, 0.47 mL, 0.75 mmol). The resulting mixture was stirred at −76° C. for 30 min, at which time a solution of WW (0.13 g, 0.36 mmol) in THF (1 mL) was added dropwise. Stirring at −76° C. was continued for 1.5 h, followed by stirring at room temperature for 1.5 h. The reaction mixture was quenched by the addition of water and saturated aqueous ammonium chloride and extracted with ethyl acetate. The combined organic extracts were washed sequentially with water and brine, dried over sodium sulfate, filtered, and concentrated under reduced pressure, and the crude residue so obtained was purified by flash chromatography (ethyl acetate/hexane) to afford XX as a yellow oil (0.14 g).

Preparation of 47: To a solution of XX (0.14 g, 0.32 mmol) in THF (3 mL) was added a solution of lithium aluminum hydride in THF (1 M, 1.3 mL, 1.3 mmol) dropwise over 10 min. The mixture was stirred and heated to reflux for 2.5 h, then cooled to 0° C. and treated with pulverized sodium sulfate decahydrate until no bubbling was noted. An aqueous solution of Rochelle's salt (1 M, 10 mL) was added, and the resulting mixture was stirred at room temperature for 16 h. Added water and extracted with dichloromethane, and the

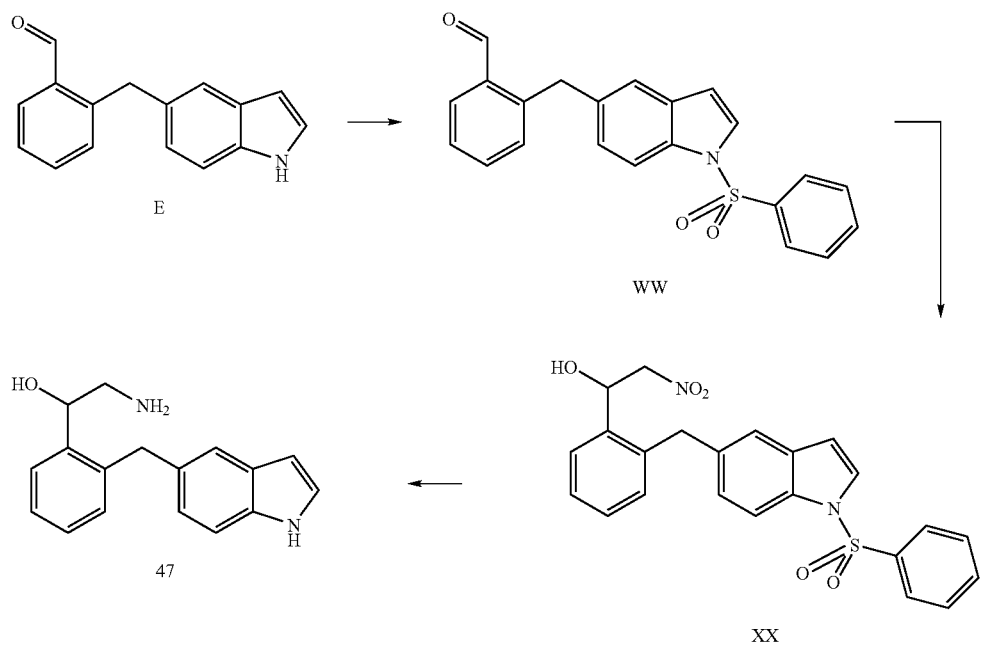

For preparation of intermediate E: see Example 2, above.
Preparation of intermediate WW: To a stirred solution of E (0.28 g, 1.2 mmol) in THF (4 mL) at 0° C. was added sodium hydride (60% dispersion, 0.14 g, 3.6 mmol), and the mixture was stirred 30 min, followed by dropwise addition of benzecombined organic extracts were dried over sodium sulfate, filtered, and concentrated under reduced pressure. The yellow oily residue so obtained was purified by flash chromatography (methanol/dichloromethane/aqueous ammonium hydroxide) to afford 47 as an off-white solid (0.023 g).

Example 17

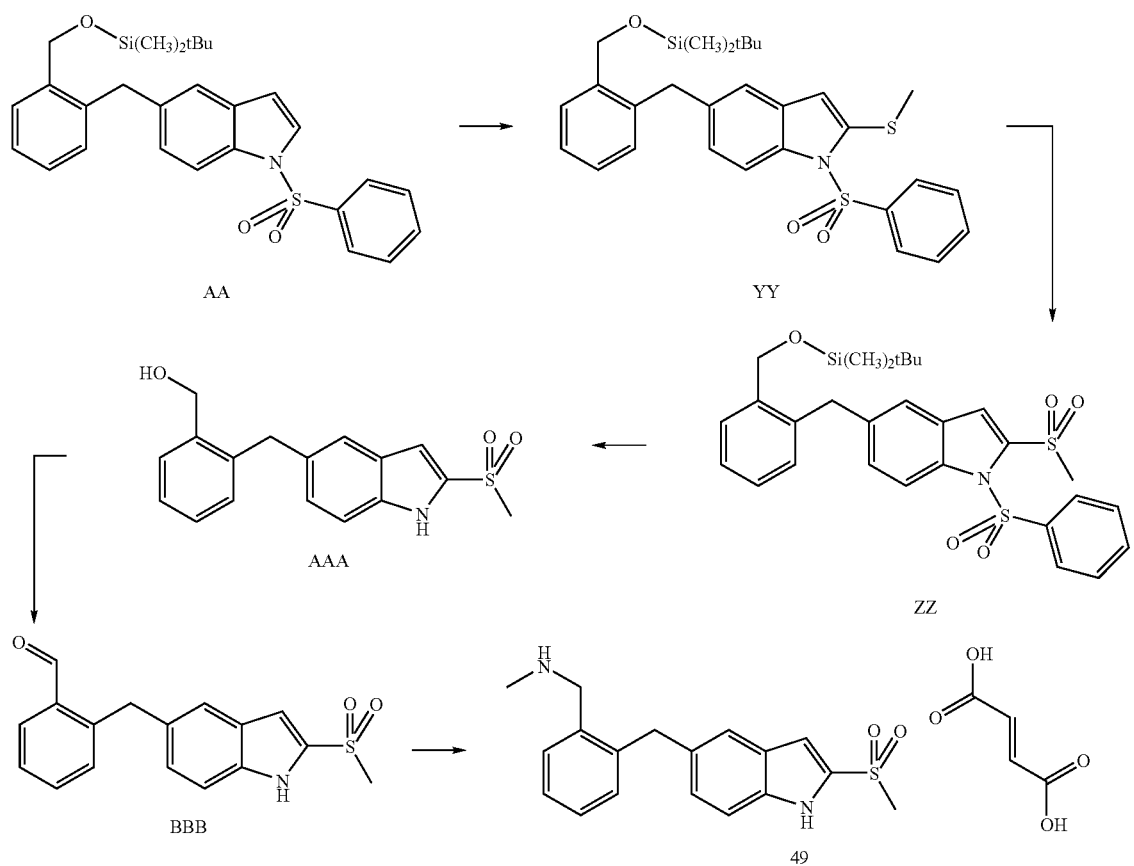

Preparation of AA: see Scheme 10, above. Preparation of intermediate YY: To a stirred solution of AA (0.64 g, 1.3 mmol) and N,N,N',N'-tetramethylethylenediamine (0.26 g, 2.2 mmol) in THF at −78° C. was added dropwise a solution of tert-butyllithium (1.7 M in pentane, 1.5 mL, 2.4 mmol). After stirring at −78° C. for 1 h, S-methyl methanethiosulfonate (0.43 g, 3.3 mmol) was added, and stirring at −78° C. was then continued for 1.5 h, followed by stirring at 0° C. for 1 h. Saturated aqueous ammonium chloride solution was added, and the reaction mixture was then diluted with water, and extracted with diethyl ether. The organic layer was washed with brine, dried over sodium sulfate, filtered, and concentrated under reduced pressure, and the crude residue so obtained was purified by flash chromatography (ethyl acetate/hexane) to afford YY (0.60 g).

Preparation of intermediate ZZ: To a solution of YY (0.60 g, 1.1 mmol) in dichloromethane (17 mL) was added meta-chloroperbenzoic acid (0.38 g, 2.2 mmol), and the resulting mixture was stirred at room temperature for 1 h. Additional meta-chloroperbenzoic acid (0.38 g, 2.2 mmol) was added, and stirring continued for 1 h. Saturated aqueous sodium bicarbonate solution was added, and the organic layer was separated, dried over sodium sulfate, filtered, and concentrated under reduced pressure. The crude residue so obtained was purified by flash chromatography (ethyl acetate/hexane) to afford ZZ as an oil (0.54 g).

Preparation of intermediate AAA: To a solution of ZZ (0.54 g, 0.95 mmol) in THF (10 mL) was added a solution of tetrabutylammonium fluoride (1.0 M in THF, 1.5 mL, 1.5 mmol), and the resulting mixture was heated at reflux for 2 h. Upon cooling to room temperature, the mixture was diluted with water and extracted with diethyl ether, and the organic layer was washed with brine, dried over sodium sulfate, filtered, and concentrated under reduced pressure. The crude residue so obtained was purified by flash chromatography (ethyl acetate/hexane) to afford AAA as a white solid (0.12 g).

Preparation of intermediate BBB: To a solution of AAA (0.12 g, 0.38 mmol) in dichloroethane (6 mL) was added activated manganese (IV) oxide (0.33 g, 3.8 mmol). The resulting black suspension was stirred at reflux for 1 h, and was filtered while still hot through a glass microfiber filter. The filtrate was concentrated under reduced pressure to afford BBB (0.12 g).

Preparation of 49: To BBB (0.12 g, 0.39 mmol) was added methylamine (33% solution in ethanol, 2 mL), and the resulting mixture was stirred for 4 h at room temperature. Sodium borohydride (0.02 g, 0.6 mmol) was added, and stirring continued for 5 min. Saturated aqueous sodium bicarbonate (0.2 mL) was added, and the crude residue was adsorbed onto silica gel and purified by flash chromatography (methanol/dichloromethane/aqueous ammonium hydroxide) to afford the free base of 49 as a light brown solid (0.12 g, 0.34 mmol), which was dissolved in methanol, treated with fumaric acid (0.042 g, 0.34 mmol) and concentrated under reduced pressure to afford 49 as a fumarate salt, an off white foam (0.16 g).

Example 18

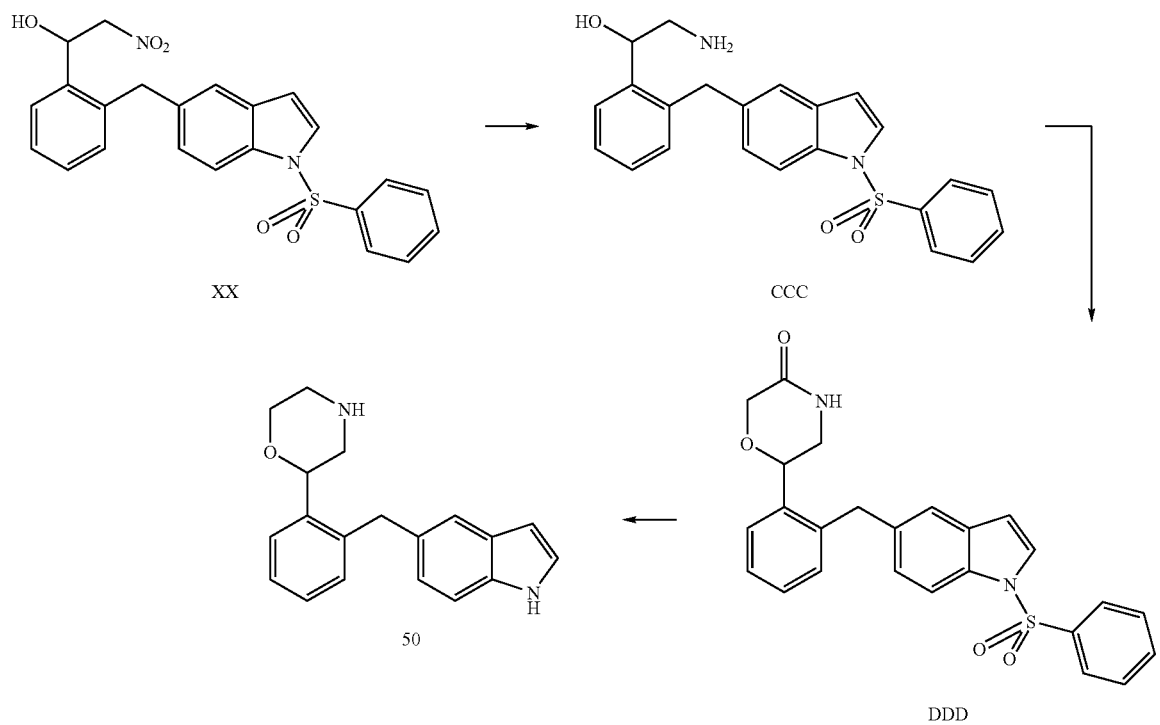

Preparation of intermediate XX: see Example 16, above.
Preparation of intermediate CCC: To a solution of XX (0.50 g, 1.1 mmol) in methanol (2.4 mL) and ethyl acetate (0.6 mL) was added 10% palladium on carbon (0.04 g), and the mixture was stirred at room temperature under a hydrogen balloon atmosphere for 16 h. The resulting mixture was filtered, concentrated under reduced pressure, and the crude residue so obtained was purified by flash chromatography (methanol/dichloromethane/aqueous ammonium hydroxide) to afford CCC as a light brown solid (0.11 g).

Preparation of intermediate DDD: To a solution of sodium hydroxide (0.013 g, 0.32 mmol) in water (1.5 mL) cooled in an ice-water bath was added chloroacetyl chloride (0.46 g, 0.53 mmol), followed by a solution of CCC (0.11 g, 0.27 mmol) in dichloromethane (1.4 mL). The reaction mixture was stirred at 0° C. for 1 h, and then was partitioned between saturated aqueous sodium bicarbonate and dichloromethane. The combined organic layers were washed with brine, dried over sodium sulfate, filtered, and concentrated under reduced pressure. The crude yellow oil so obtained was dissolved in THF (3 mL), cooled to 0° C., and then sodium hydride (0.012 g of 60% dispersion) was added. The resulting mixture was stirred at 0° C. for 3 h and then at room temperature for 4 h, and then was partitioned between saturated aqueous sodium bicarbonate and dichloromethane. The combined organic layers were washed with brine, dried over sodium sulfate, filtered, and concentrated under reduced pressure. The crude residue so obtained was purified by flash chromatography (methanol/dichloromethane/aqueous ammonium hydroxide) to afford DDD as a yellow oil (0.033 g).

Preparation of 50: To a solution of DDD (0.033 g, 0.074 mmol) in THF (1 mL) was added a solution of lithium aluminum hydride in THF (1 M, 0.4 mL, 0.4 mmol) dropwise over 10 min. The mixture was stirred and heated to reflux for 16 h, then cooled to 0° C. and treated with a saturated aqueous solution of Rochelle's salt (5 mL) and with dichloromethane (5 mL), and the resulting mixture was stirred at room temperature for 2 h. Additional saturated aqueous solution of Rochelle's salt (5 mL) was added, and the mixture was extracted with dichloromethane, and the combined organic extracts were dried over sodium sulfate, filtered, and concentrated under reduced pressure. The crude residue so obtained was purified by flash chromatography (methanol/dichloromethane/aqueous ammonium hydroxide) to afford 50 as a yellow oil (0.011 g).

Formulations

Example 19

Pharmaceutical preparations for delivery by various routes are formulated as shown in the following Tables. "Active ingredient" or "Active compound" as used in the Tables means one or more of the Compounds of Formulae I-II.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 20

Screening for Human Serotonin Transporter (hSERT) Antagonists Using a Scintillation Proximity Assay (SPA)

The screening assay of this example was used to determine the affinity of ligands at the hSERT transporter by competition with [$^3$H]-Citalopram.

Scintillation Proximity Assay (SPA) works by bringing radioligand within close proximity to the bead's scintillant to stimulate light emission. In this assay, the receptor-containing membranes were pre-coupled to the SPA beads and the binding of the appropriate radioligand to the transporter was measured. The light emission was proportional to the amount of bound radioligand. Unbound radioligand produced no signal as a result of distant proximity to scintillant (lack of energy transfer).

HEK-293 cells (Tatsumi et al., Eur. J. Pharmacol. 1997, 30, 249-258) stably expressing recombinant hSERT were maintained with media (DMEM high glucose with 10% FBS, 300 µg/ml G418 and 2 mM L-Glutamine) and incubated at 37° C. with 5% $CO_2$. Cells are released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3 mg/ml (w:v). and stored at −80° C.

For Scintillation Proximity Assay $IC_{50}/K_i$ determination, 50 mM Tris-HCl and 300 mM NaCl, (pH 7.4) buffers were utilized. Compounds of the invention were diluted from 10 mM to 0.1 nM FAC (10 point curves, whole log/half log dilutions) via a Beckman Biomek 2000 using a serial dilution protocol. The test compounds were then transferred (20 µl/well) and the [$^3$H]-Citalopram radioligand was added at 50 µl/well. Membrane and beads were prepared to a ratio of 10 µg: 0.7 mg, with 0.7 mg PVT-WGA Amersham beads (Cat#RPQ0282V) added per well. 130 µl of the membrane : bead mixture was added to the assay plate. The mixtures were allowed to stand at room temperature for one hour, and were then counted on a Packard TopCount LCS, a generic Scintillation Proximity Assay counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound counts per minute (CPM) at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for human serotonin transporter. For example, 5-(2-Methylaminomethyl-benzyl)-1H-indole-3-carbonitrile exhibited a pKi of approximately 10.0 using the above assay.

Example 21

Screening for Compounds Active at Human Norepinephrine Transporter (hNET) Using a Scintillation Proximity Assay (SPA)

This assay was used to determine the affinity of ligands for the hNET transporter by competition with [$^3$H]-Nisoxetine. As in the hSERT assay of the above example, receptor-containing membranes were pre-coupled to the SPA beads and the binding of the appropriate radioligand to the transporter was measured. The light emission was proportional to the amount of bound radioligand, with unbound radioligand producing no signal.

HEK-293 cells (Tatsumi et al., Eur. J. Pharmacol. 1997, 30, 249-258) stably expressing recombinant hNET (Clone: HEK-hNET #2) were maintained with media (DMEM hi glucose with 10% FBS, 300 µg/ml G418 and 2 mM L-Glutamine) and incubated at 37° C. with 5% $CO_2$. Cells were released from culture flasks using PBS for 1-2 minutes. The cells were subsequently centrifuged at 1000 g's for 5 minutes and resuspended in PBS prior to being used in the membrane preparation.

Cell membranes were prepared using a membrane preparation buffer of 50 mM TRIS (pH 7.4). Cell membranes were prepared from a single cube (7.5×10$^9$ cells total). Cells were homogenized using a Polytron (setting medium for a 4 second burst). The homogenate was then centrifuged at 48,000×g for 15 minutes, the supernatant subsequently removed and discarded, and the pellet resuspended with fresh buffer. After a second centrifugation, the pellet was re-homogenized and brought to a final volume determined during the assay. Typically, membrane portions were aliquoted in 3-6 mg/ml (w:v). and stored at −80° C.

$^3$[H] Nisoxetine radioligand (Amersham Cat. #TRK942 or Perkin Elmer Cat. #NET1084, specific activity: 70-87 Ci/mmol, stock concentration: 1.22e−5 M, final concentration: 8.25e−9 M), and 50 mM Tris-HCl, 300 mM NaCl, (pH 7.4) buffers were used for Scintillation Proximity Assay $IC_{50}$/$K_i$ determination. Compounds of the invention were diluted from 10 mM to 0.1 InM FAC (10 point curves, whole log/half log dilutions) via a Beckman Biomek 2000 using a serial dilution protocol. The test compounds were then transferred (20 µl/well) and the radioligand was added at 50 µl/well. Membrane and beads were prepared to a ratio of 10 µg: 0.7 mg, with 0.7 mg PVT-WGA Amersham beads (Cat#RPQ0282V) added per well. 130 µl of the membrane: bead mixture was added to the assay plate. The mixtures were allowed to stand at room temperature for one hour, and were then counted on a Packard TopCount LCS, a generic SPA counting protocol settings (Energy Range: Low, Efficiency Mode: Normal, Region A: 1.50-35.00, Region B: 1.50-256.00, Count Time (min.): 0.40, Background Subtract: none, Half-Life Correction: no, Quench Indicator: tSIS, Platemap blank subtraction: No, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human norepinephrine transporter. For example, 5-(2-Methylaminomethyl-benzyl)-1H-indole-2-carboxylic acid amide exhibited a pKi of approximately 8.4 using the above assay.

Example 22

Screening for Compounds Active at Human Dopamine Transporter (hDAT) Using a Scintillation Proximity Assay (SPA)

This assay was used to determine the affinity of ligands for the dopamine transporter by competition with [$^3$H]-Vanoxerine.

HEK-293 cells (Tatsumi et al., Eur. J. Pharmacol. 1997, 30, 249-258) stably expressing recombinant hDAT were maintained with media (DMEM hi glucose with 10% FBS, 300 µg/ml G418 and 2 mM L-Glutamine) and incubated at 37° C. with 5% $CO_2$. Cells were plated four hours prior to experiment by placing approximately 30,000 cells per well (in PBS) on white, opaque Cell-Tak coated 96 well plates. Extra buffer was apriated from the cell plates using an ELx405 plate washer.

$^3$[H] vanoxerine (GBR 12909) radioligand, specific activity approximately 59 Ci/mmol, stock concentration, 400 nM, and 50 mM Tris-HCl, 300 mM NaCl, (pH 7.4) buffers were used for Scintillation Proximity Assay $IC_{50}/K_i$ determination. Compounds of the invention were diluted from 10 mM to 0.1 nM FAC (10 point curves, whole log/half log dilutions) via a Beckman Biomek 2000 using a 10-point dilution protocol. The mixtures were allowed to stand at room temperature for 30 minutes, and were then counted on a Packard TopCount LCS, a generic SPA counting protocol settings, Count Time (min.): 0.40, Background Subtract: none, Half-Life Correction: none, Quench Indicator: tSIS, Platemap blank subtraction: none, Cross talk reduction: Off).

The % inhibition was calculated for each compound tested [(Compound CPM at maximum concentration-Non-Specific CPM)/Total CPM*100]. The concentration producing 50% inhibition ($IC_{50}$) was determined using an iterative non-linear curve fitting technique with Activity Base/Xlfit using the following equation:

$$y = \frac{\max - \min}{1 + (IC50/x)^n} + \min$$

where max=total binding, min=non specific binding, x=concentration (M) of the tested compound and n=Hill slope. The inhibition dissociation constant (Ki) of each compound was determined according to the method of Cheng-Prusoff and then converted into negative logarithm (pKi) of the Ki.

Using the above procedure, compounds of the invention were found to have affinity for the human dopamine transporter. For example, 5-(2-Methylaminomethyl-benzyl)-1H-indole-2-carboxylic acid amide exhibited a pKi of approximately 8.3 using the above assay.

Example 23

Formalin Pain Assay

Male Sprague Dawley rats (180-220 g) are placed in individual Plexiglas cylinders and allowed to acclimate to the testing environment for 30 min. Vehicle, drug or positive control (morphine 2 mg/kg) is administered subcutaneously at 5 ml/kg. 15 min post dosing, formalin (5% in 50 µl) is injected into plantar surface of the right hind paw using a 26-gauge needle. Rats are immediately put back to the observation chamber. Mirrors placed around the chamber allow unhindered observation of the formalin-injected paw. The duration of nociphensive behavior of each animal is recorded by a blinded observer using an automated behavioral timer. Hindpaw licking and shaking/lifting are recorded separately in 5 min bin, for a total of 60 min. The sum of time spent licking or shaking in seconds from time 0 to 5 min is considered the early phase, whereas the late phase is taken as the sum of seconds spent licking or shaking from 15 to 40 min. A plasma sample is collected.

Example 24

Colon Pain Assay

Adult male Sprague-Dawley rats (350-425 g; Harlan, Indianapolis, Ind.) are housed 1-2 per cage in an animal care facility. Rats are deeply anesthetized with pentobarbital sodium (45 mg/kg) administered intraperitoneally. Electrodes are placed and secured into the external oblique musculature for electromyographic (EMG) recording. Electrode leads are tunneled subcutaneously and exteriorized at the nape of the neck for future access. After surgery, rats are housed separately and allowed to recuperate for 4-5 days prior to testing.

The descending colon and rectum are distended by pressure-controlled inflation of a 7-8 cm-long flexible latex balloon tied around a flexible tube. The balloon is lubricated, inserted into the colon via the anus, and anchored by taping the balloon catheter to the base of the tail. Colorectal distension (CRD) is achieved by opening a solenoid gate to a constant pressure air reservoir. Intracolonic pressure is controlled and continuously monitored by a pressure control device. Response is quantified as the visceromotor response (VMR), a contraction of the abdominal and hindlimb musculature. EMG activity produced by contraction of the external oblique musculature is quantified using Spike2 software (Cambridge Electronic Design). Each distension trial lasts 60 sec, and EMG activity is quantified for 20 sec before distension (baseline), during 20 sec distension, and 20 sec after distention. The increase in total number of recorded counts during distension above baseline is defined as the response. Stable baseline responses to CRD (10, 20, 40 and 80 mmHg, 20 seconds, 4 minutes apart) are obtained in conscious, unsedated rats before any treatment.

Compounds are evaluated for effects on responses to colon distension initially in a model of acute visceral nociception and a model of colon hypersensitivity produced by intracolonic treatment with zymosan (1 mL, 25 mg/mL) instilled into the colon with a gavage needle inserted to a depth of about 6 cm. Experimental groups will consist of 8 rats each.

Acute visceral nociception: For testing effects of drug on acute visceral nociception, 1 of 3 doses of drug, vehicle or positive control (morphine, 2.5 mg/kg) are administered after baseline responses are established; responses to distension are followed over the next 60-90 minutes.

Visceral hypersensitivity: For testing effects of drug or vehicle after intracolonic treatment with zymosan, intracolonic treatment is given after baseline responses are established. Prior to drug testing at 4 hours, responses to distension are assessed to establish the presence of hypersensitivity. In zymosan-treated rats, administration of 1 of 3 doses of drug, vehicle or positive control (morphine, 2.5 mg/kg) are given 4 hours after zymosan treatment and responses to distension followed over the next 60-90 minutes.

Example 25

Cold Allodynia in Rats With a Chronic Constriction Injury of the Sciatic Nerve

The effects of compounds of this invention on cold allodynia are determined using the chronic constriction injury (CCI) model of neuropathic pain in rats, where cold allodynia is measured in a cold-water bath with a metal-plate floor and water at a depth of 1.5-2.0 cm and a temperature of 3-4° C. (Gogas, K. R. et al., Analgesia, 1997, 3, 1-8).

Specifically, CCI, rats are anesthetized; the trifurcation of the sciatic nerve is located and 4 ligatures (4-0, or 5-0 chromic gut) are placed circumferentially around the sciatic nerve proximal to the trifurcation. The rats are then allowed to recover from the surgery. On days 4-7 after surgery, the rats are initially assessed for cold-induced allodynia by individually placing the animals in the cold-water bath and recording the total lifts of the injured paw during a 1-min period of time: The injured paw is lifted out of the water. Paw lifts associated with locomotion or body repositioning are not recorded. Rats that displayed 5 lifts per min or more on day 4-7 following surgery are considered to exhibit cold allodynia and are used in subsequent studies. In the acute studies, vehicle, reference compound or compounds of this invention are administered subcutaneously (s.c.) 30 min before testing. The effects of repeated administration of the compounds of this invention on cold allodynia are determined 14, 20 or 38 h following the last oral dose of the following regimen: oral (p.o.) administration of vehicle, reference or a compound of this invention at ~12 h intervals (BID) for 7 days.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of Formula I:

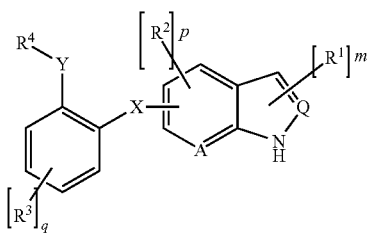

or a pharmaceutically acceptable salt thereof,
wherein:
X is $CH_2$;
Y is $(CH(R^5))_n$;
n is 0, 1, or 2;
Q is CH;
A is CH;
$R^1$ and $R^2$ are each independently CN, $C(O)NH_2$, $S(O)_2R^{1'}$, halogen, lower alkyl, lower haloalkyl, or lower alkoxy;
$R^{1'}$ is H or lower alkyl;
m is 0 or 1;
p is 0, 1, or 2;
$R^3$ is lower alkyl, lower alkoxy, lower haloalkyl, halogen, CN, $C(O)N(R^{1'})_2$, $NHS(O)_2R^{1'}$, or $N(R^{3'})(R^{3''})$;
$R^{3'}$ and $R^{3''}$ are each independently H, lower alkyl, lower haloalkyl, or $R^{3'}$ and $R^{3''}$ together form lower heteroaryl or lower heterocycloalkyl, optionally substituted with lower alkyl, hydroxy, lower alkoxy, lower haloalkyl, or oxo;
q is 0, 1, or 2;
$R^4$ is $N(R^{4'})(R^{4''})$;

$R^{4'}$ and $R^{4''}$ are each independently H, lower alkyl, lower hydroxyalkyl, lower alkoxyalkyl, lower cycloalkyl, lower haloalkyl; and
each $R^5$ is independently H, lower alkyl, lower alkoxy, lower hydroxyalkyl, or lower haloalkyl.

2. A compound according to claim 1 selected from the group consisting of:
[2-(1H-Indol-5-ylmethyl)-benzyl]-methyl-amine;
1-[2-(1H-Indol-5-ylmethyl)-phenyl]-ethylamine;
{(R)-1-[2-(1H-Indol-5-ylmethyl)-phenyl]-ethyl}-methyl-amine;
{(S)-1-[2-(1H-Indol-5-ylmethyl)-phenyl]-ethyl}-methyl-amine;
[2-(1H-Indol-5-ylmethyl)-3-methoxy-benzyl]-methyl-amine;
[3-Fluoro-2-(1H-indol-5-ylmethyl)-benzyl]-methyl-amine;
[2-(7-Fluoro-1H-indol-5-ylmethyl)-benzyl]-methyl-amine;
[2-(1H-Indol-5-ylmethyl)-6-methoxy-benzyl]-methyl-amine;
[2-(1H-Indol-5-ylmethyl)-3-trifluoromethyl-benzyl]-methyl-amine;
[2-(1H-Indazol-5-ylmethyl)-benzyl]-methyl-amine;
2-(1H-Indol-5-ylmethyl)-phenylamine;
[2-(1H-Indol-6-ylmethyl)-benzyl]-methyl-amine;
[2-(1H-Indol-5-ylmethyl)-benzyl]-dimethyl-amine;
Ethyl-[2-(1H-indol-5-ylmethyl)-benzyl]-amine;
[5-Fluoro-2-(1H-indol-5-ylmethyl)-benzyl]-methyl-amine;
2-[2-(1H-Indol-5-ylmethyl)-benzylamino]-ethanol;
Cyclopropyl-[2-(1H-indol-5-ylmethyl)-benzyl]-amine;
2-(1H-Indol-5-ylmethyl)-benzylamine;
[5-Chloro-2-(1H-indol-5-ylmethyl)-benzyl]-methyl-amine;
{2-[2-(1H-Indol-5-ylmethyl)-phenyl]-ethyl}-methyl-amine;
5-(2-Methylaminomethyl-benzyl)-1H-indole-3-carbonitrile;
5-(2-Methylaminomethyl-benzyl)-1H-indole-3-carboxylic acid amide;
[3-(1H-Indol-5-ylmethyl)-benzyl]-methyl-amine;
[2-(1H-Indol-5-ylmethyl)-4-methoxy-benzyl]-methyl-amine;
[2-(1H-Indol-5-ylmethyl)-5-methoxy-benzyl]-methyl-amine;
[2-(1H-Indol-5-ylmethyl)-benzyl]-(2,2,2-trifluoro-ethyl)-amine;
5-(2-Methylaminomethyl-benzyl)-1H-indole-2-carbonitrile;
4-(1H-Indol-5-ylmethyl)-3-methylaminomethyl-benzonitrile;
5-(2-Methylaminomethyl-benzyl)-1H-indole-2-carboxylic acid amide;
N-[4-(1H-Indol-5-ylmethyl)-3-methylaminomethyl-phenyl]-methanesulfonamide;
3-(1H-Indol-5-ylmethyl)-4-methylaminomethyl-benzonitrile;
3-(1H-Indol-5-ylmethyl)-4-methylaminomethyl-benzamide;
2-Amino-1-[2-(1H-indol-5-ylmethyl)-phenyl]-ethanol; and
[2-(2-Methanesulfonyl-1H-indol-5-ylmethyl)-benzyl]-methyl-amine.

3. A pharmaceutical composition comprising the compound of claim 1 and a pharmaceutically acceptable carrier.

4. The compound of claim 1 wherein Y is $(CH(R^5))_n$ and n is 1.

5. The compound of claim 4, wherein $R^5$ is H.

6. The compound of claim 5, wherein $R^{4'}$ is H.

7. The compound of claim 4, wherein q is 0.

8. The compound of claim 4, wherein m is 0.

9. The compound of claim 6, wherein $R^{4''}$ is lower alkyl.

10. The compound of claim 4, wherein q is 1.

11. The compound of claim 4, wherein $R^3$ is halogen.

12. The compound of claim 4, wherein $R^3$ is lower alkoxy or lower haloalkyl.

\* \* \* \* \*